(12) United States Patent
Williams et al.

(10) Patent No.: US 6,406,427 B1
(45) Date of Patent: Jun. 18, 2002

(54) BRAIN RESCUE INSTRUMENT AND METHOD

(75) Inventors: Christopher E. Williams; Mark I. Gunning, both of Auckland (NZ)

(73) Assignee: Auckland Uniservices Limited, Auckland (NZ)

(*) Notice: Subject to any disclaimer, the term of this patent is extended or adjusted under 35 U.S.C. 154(b) by 0 days.

(21) Appl. No.: 09/445,760
(22) PCT Filed: Jun. 10, 1998
(86) PCT No.: PCT/NZ98/00083
§ 371 (c)(1),
(2), (4) Date: Feb. 18, 2000
(87) PCT Pub. No.: WO98/57139
PCT Pub. Date: Dec. 17, 1998

(30) Foreign Application Priority Data

Jun. 10, 1997 (NZ) .................................................. 328047

(51) Int. Cl.[7] .................................................. A61B 5/00
(52) U.S. Cl. ..................................................... 600/301
(58) Field of Search .................................. 600/301, 513, 600/544

(56) References Cited

U.S. PATENT DOCUMENTS 5,623,925 A * 4/1997 Swenson et al.
5,730,146 A * 3/1998 Itil et al.

* cited by examiner

Primary Examiner—Scott M. Getzow

(57) ABSTRACT

An intelligent brain rescue instrument for identifying, monitoring, and guiding the application of brain therapies to patients with evolving brain injuries, includes an input for acquiring a multiple number of signals each indicative of a different biochemical or biophysical parameter of a patient, a computer to continuously sample each of the acquired signals and display to a user on a monitor at least some of the parameters, the displayed parameters being selected by system software embodying expert analytical rules as the most significant parameters, or as parameters having values indicative, or predictive at any time of actual, or potential future deterioration of the brain state of the patient.

48 Claims, 19 Drawing Sheets

(a) Infarction rate
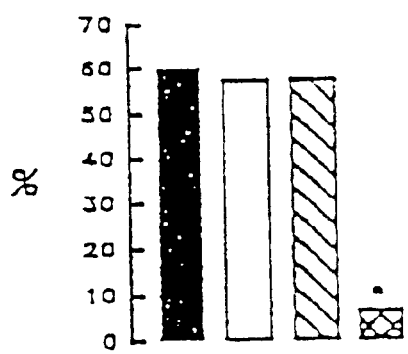
(b) Area of cortical infarction
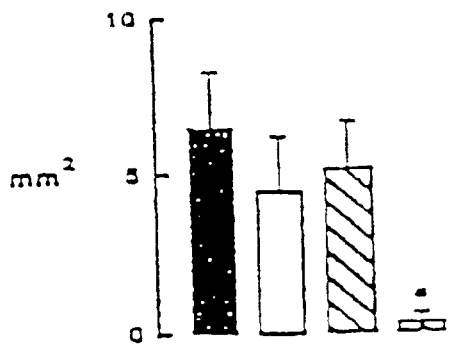
(c) Surviving hippocampal neurons
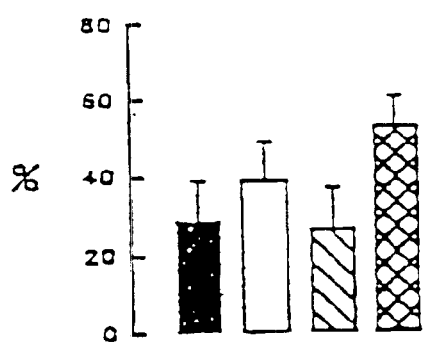
(d) Striatal neuronal loss score
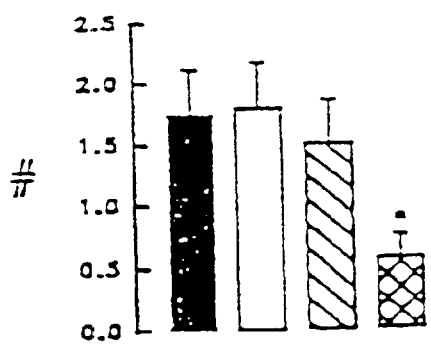
(e) Area of cortical infarction 3 weeks after hypoxia
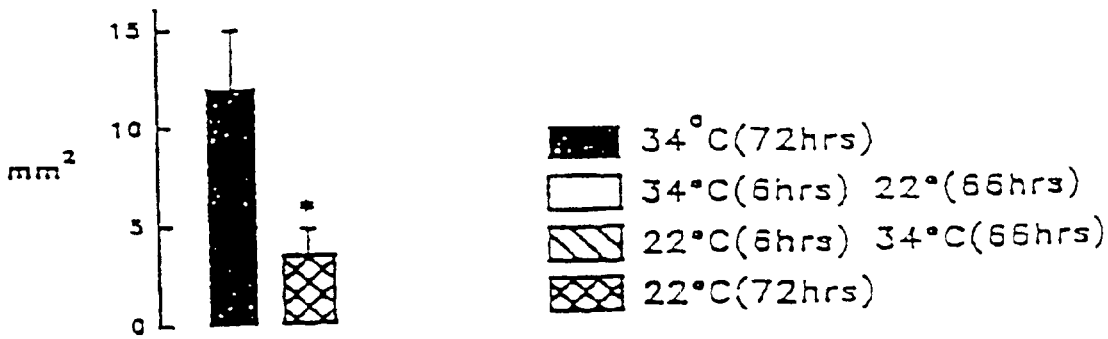
- 34°C(72hrs)
- 34°C(6hrs) 22°(66hrs)
- 22°C(6hrs) 34°C(66hrs)
- 22°C(72hrs)
Figure 7

Magnitude of drop in blood pressure, and levels of lactate and glucose versus neural outcome. (r = correlation coefficient; p = significance.

|  | r | p |
|---|---|---|
| CA3 neuronal loss vs % blood pressure drop | 0.876 | p=0.02 |
| CA1/2 neuronal loss vs % blood pressure drop | 0.922 | p=0.01 |
| CA3 neuronal loss vs lactate 10 min after insult. | 0.035 | NS |
| CA3 neuronal loss vs lactate 1 hr after insult. | -0.066 | NS |
| CA3 neuronal loss vs glucose - 10 min insult | 0.512 | NS |

Correlations between total neuronal loss score and measured changes during the 4th umbilical cord occlusion.

|  | r | p |
|---|---|---|
| HR (% of baseline) | 0.28 | 0.54 |
| MAP (% of baseline) | 0.867 | 0.01 |
| T/QRS ratio of ECG | 0.75 | 0.03 |
| PpO$_2$ (kPa) | 0.5 | 0.26 |
| pH | -0.71 | 0.08 |
| Lactate (mM/L) | 0.49 | 0.26 |
| Glucose (mM/L) | 0.13 | 0.78 |
| EEG depression (min) | 0.78 | 0.02 |
| No. of seizures | 0.95 | <0.01 |

Figure 12

| A | Hypoperfusion at +10 min | Hyperperfusion at +24 h |
|---|---|---|
| Cortical Neuronal Loss (%) | r=0.65<br>p<0.001<br>α= -0.70 | r=0.67<br>p=0.007<br>α= -0.50 |

BRAIN RESCUE INSTRUMENT AND METHOD

FIELD OF INVENTION

This invention relates particularly to data evaluation equipment and procedures for the monitoring and management of brain injuries in mammals.

BACKGROUND

The brain can be compromised by a number of adverse influences during all stages of life including perinatal asphyxial and hypoperfusion insults, strokes, traumatic brain injuries, cardiac arrest, cardiac bypass surgery, poisoning, and subarachnoid haemorrhages. Considerable variation occurs in the degree and distribution of neuronal loss depending on the type and severity of the injury to the brain.

Injury results in two recognised phases of neuronal loss (see FIG. 16 of the. accompanying figures): primary neuronal death is associated with the insult itself, and delayed neuronal death occurs during a secondary phase some hours later, when a complex pathological cascade of events leading to neuronal death follows the initial injury. A transient insult, such as hypoperfusion, can cause brain cells to die in two phases. The primary phase extends throughout the insult and the early regeneration/reperfusion period. Processes contributing to this primary phase include intracellular $Na^+$ and $Ca^{2+}$ accumulation, cytotoxic edema, membrane damage, free radicals, and excitotoxicity. However, many neurons do not necessarily die during the primary phase but cytotoxic mechanisms are triggered that lead to a further or delayed death of neurons some hours later. The mechanisms involved in delayed neuronal death are thought to include excitoxicity, seizures, apoptosis, and microglial activation.

Recent studies suggest that it is possible to interfere with these mechanisms and thereby rescue susceptible neurons. Biophysical measures of the pathophysiologic processes preceding and during the phases of neuronal death are likely to prove useful for identifying those patients who may benefit from neuronal rescue therapies. Several clinically relevant factors such as pre-existing injuries, hypotension or metabolic. status may sensitise and alter the response of the brain to injury. Several biophysical parameters recorded during and after an insult are generally needed to reliably discriminate the present phase of injury and periods of cytotoxic activity.

The monitoring of patients with brain injuries whether caused by externally induced trauma such as birth or accident or by circulatory problems or poisoning has hitherto relied upon clinical signs but these may not be observable until a time at which the damage may have become irreversible. Neurological examination is of limited value (in particular for those on life support apparatus) for predicting outcome and determining the phase of injury. Similarly, use of imaging techniques such as MRI and CT are not practical for monitoring evolving injuries in these patients.

SUMMARY OF INVENTION

The invention provides an intelligent monitoring instrument, termed a brain rescue instrument or monitor, and method, for monitoring, identifying and guiding the application of brain therapies to patients, with evolving brain injuries, and generally for assisting with the management and treatment of brain injury in a mammalian patient.

In broad terms in one aspect the invention comprises an intelligent brain rescue instrument for identifying, monitoring, and guiding the application of brain therapies to patients with evolving brain injuries, comprising:

input means for acquiring a multiple number of signals each indicative of a different biochemical or biophysical parameter of a patient, and computing means configured to continuously sample and process each of the acquired signals and display to a user on a monitor at least some of the parameters, the displayed parameters being selected by system software embodying expert analytical rules as the most significant parameters or as parameters having values indicative or predictive at any time of actual or potential future deterioration of the brain state of the patient.

In broad terms in another aspect the invention comprises an intelligent brain rescue instrument for identifying, monitoring, and guiding the application of brain therapies to patients with evolving brain injuries, comprising:

I) input means for acquiring a set of a multiple number of signals each indicative of a different biochemical or biophysical parameter of the patient, said set of signals being selected from:
  (a) an EEG signal;
  (b) an ECG signal;
  (c) a signal indicative of brain tissue impedance of the patient;
  (d) signal or signals indicative of the temperature of the patient;
  (e) signals indicative of the arterial blood pressure and/or arterial oxygen saturation, of the patient;
  (f) a signal indicative of intracranial pressure;
  (g) a signal or signals indicative of any of cerebral blood flow, cerebral blood volume, cerebral oxygenation, or cerebral metabolite measures;
  (h) a signal or signals indicative of systemic glucose concentration and/or central glucose concentration;
  (i) a signal or signals indicative of systemic lactate concentration and/or central lactate concentration;
  (j) a signal indicative of cerebrovascular status;
  (k) a signal indicative of cerebral cytochrome levels;
  (l) a signal indicative of the patient's heart rate;
  (m) a signal indicative of central cytotoxic activity;
  (n) a signal or signals indicative of movement or muscle activity;
  (o) a signal or signals indicative of any other biochemical or biophysical parameter useful as indicative of the current or as predictive of the future brain state of the patient; and II) computing means configured to:
  (a) continuously sample and process each of the acquired signals; and
  (b) display to a user on a monitor information a selected subset of the acquired parameters, said selected subset of parameters which is displayed being selected either by system software embodying expert analytical rules as the most significant parameters or as parameters having values indicative or predictive at any time of actual or potential deterioration of the brain state of the patient, with said parameters being displayed against a scale or scales or in a way which highlights to a clinician any variations of the parameters indicative or predictive of the deterioration of the brain state of the patient, or alternatively being override selected at any time by the user.

In broad terms in a further aspect the invention comprises a method for identifying, monitoring, and guiding the application of brain therapies to patients with evolving brain injuries, comprising acquiring a multiple number of signals each indicative of a different biochemical or biophysical parameter of a patient, and via computing means continuously sampling each of the acquired signals and displaying to a user on a monitor at least some of the parameters, the displayed parameters being selected by system software embodying expert analytical rules as parameters having values indicative or predictive at any time of actual or potential future deterioration of the brain state of the patient, with said parameters being displayed against a scale or scales or in a way which highlights to a clinician variations of the parameters indicative or predictive of deterioration in the brain state of the patient.

The brain rescue instrument monitors at least some of the pathophysiologic and temporal events surrounding encephalopathies - which events are predictive of pathological neuronal death or can influence the degree of secondary injury. This information is a prerequisite to deciding whether or not intervention with neuronal rescue therapy is indicated. The invention enables a better detection procedure for predicting the secondary loss of brain cells, so that steps to alleviate secondary injury may be taken as soon as possible and even before the appearance of clinical signs, to achieve increased survival and better long-term prospects of patients.

BRIEF DESCRIPTION OF THE FIGURES

The invention will be further described with reference to the accompanying drawings in which.

DETAILED DESCRIPTION OF PREFERRED FORM

The preferred form brain rescue monitor samples, processes, data reduces, stores and evaluates various biochemical and biophysical parameters of relevance to the management of an individual patient with brain injury. The system comprises system software embodying expert analytical rules for managing signal handling and for signal analysis. The system displays information on some of those which are monitored, which are those most significant for the patient type and/or injury type, against a scale in a way which highlights any variations in the parameters indicative or predictive of deterioration in the brain state of the patient. The system monitors other input signals in background, and provides an indication to the user if any of those background signals or parameters varies to indicate a deterioration of the brain state of the patient. The indication may be by a pop up window which displays information concerning the previously background parameter, or other warning to the user. The collection of all of the information may be used by a physician in the monitoring and management of brain injuries and guiding the application of brain rescue therapies.

The system hardware of the preferred form brain rescue monitor comprises an embedded microprocessor with associated data acquisition stages to which electrodes or sensors connected to the patient, other instrumentation, or any other signal sources are connected. A screen displays information on selected monitored parameters.

Figure 1:
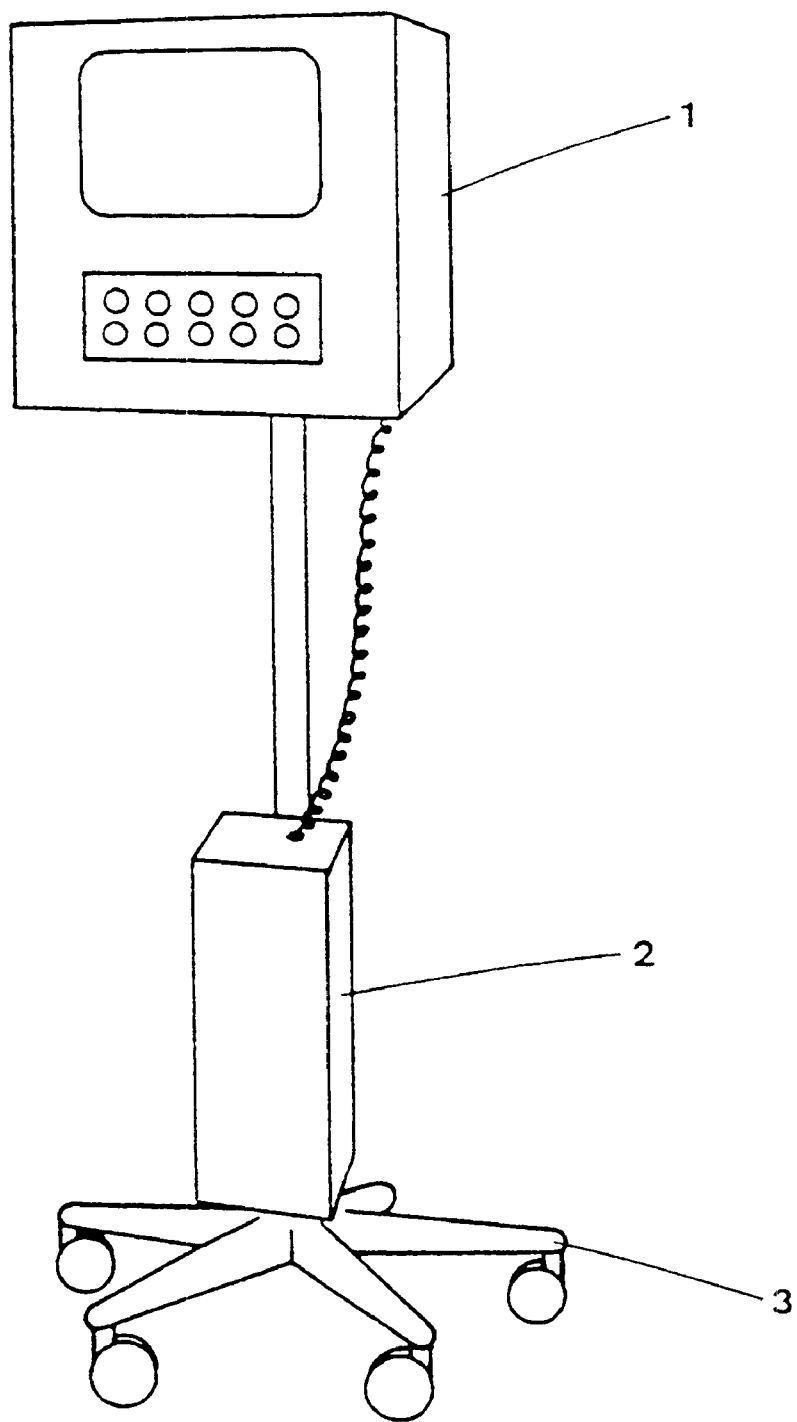
FIG. 1 is a view of a preferred form trolley mounted brain rescue monitor of the invention.

Referring to FIG. 1, the preferred form brain rescue monitor unit 1 is carried on a rolling stand 2 having an internal pneumatic spring which allows the unit 1 to be adjusted at to different heights at a patient's bedside, for example. A battery 3 is, in the preferred form, mounted to the base of the stand as shown, either as the primary power source for the unit or as a back up to mains power to ensure reliable operation. In alternative forms the unit may be wall mounted, otherwise bedside mounted, or even formed as a smaller unit which is attached to the patient's head or body for example.

Figure 2:
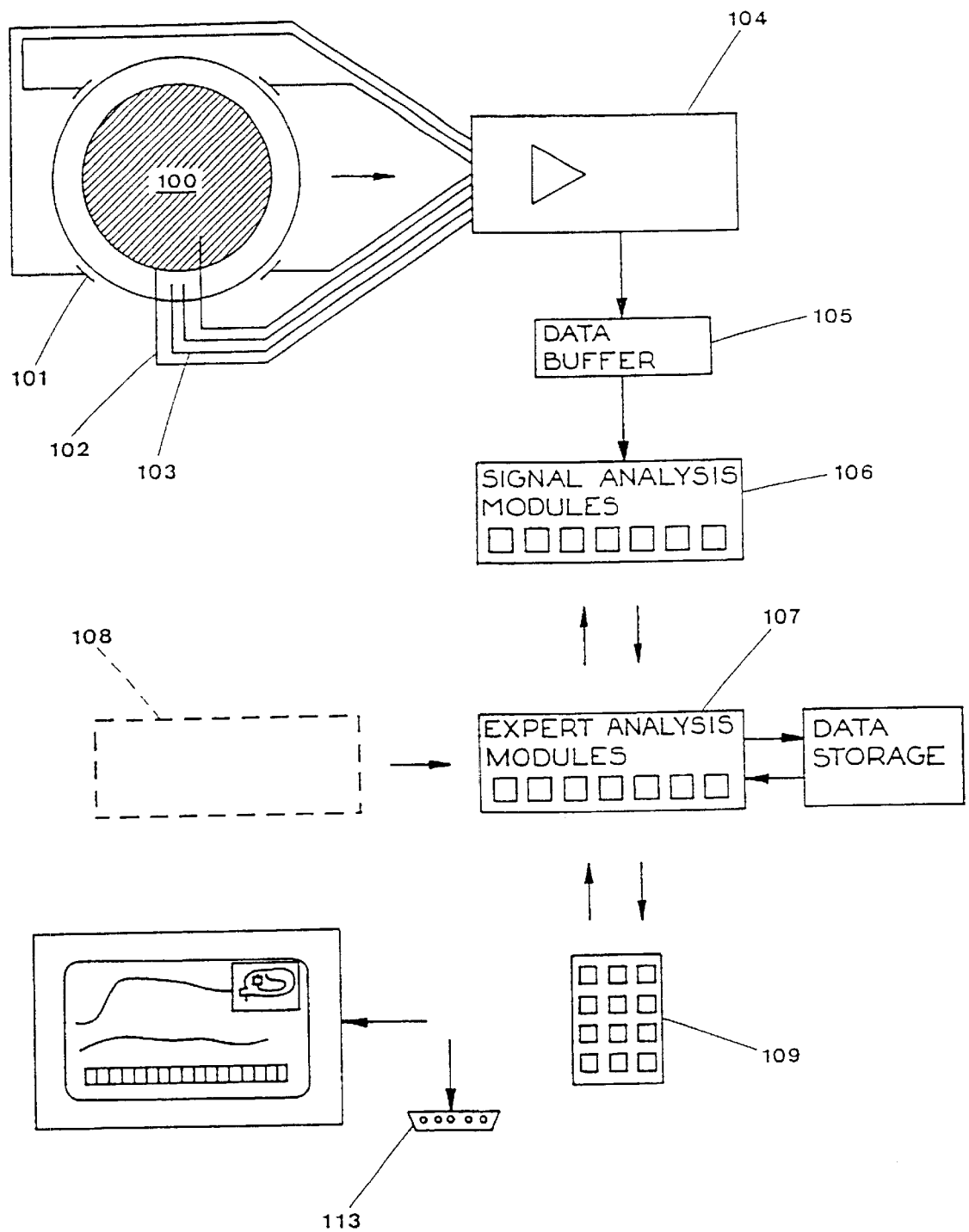
FIG. 2 shows an overview of the hardware and software systems of the preferred from brain rescue monitor.

FIG. 2 shows the major components of the preferred form system. The preferred form system has input channels and data acquisition electronics for an EEG signal, an ECG signal, a cortical impedance signal, cerebral and core temperature signals, arterial blood pressure and arterial oxygen saturation signals, an intracranial pressure signal, cerebral blood flow, cerebral blood volume, cerebral oxygenation and cerebral metabolic signals, systemic glucose concentration and central glucose concentration signals, a cerebrovascular status signal, central cytochrome levels, heart rate, central cytotoxic activity, patient movement or muscle activity. A number of these input signals such as EEG, ECG, cortical impedance, intracranial pressure, near infrared spectroscopy, microdialysis analyses and temperature sensors are obtained as is known in the art via sensors attached to or within the patient's head. A number of parameters can be sensed through EEG electrodes such as the EEG itself, seizure and spike activity, and cerebral impedance, and an ECG. In some cases, data for one input parameter can be extracted from input data on one or a number of other input parameters, eg heart rate can be extracted from blood pressure, ECG, and pulse oximetery. In general, sensors used to obtain input signals may include fiberoptic leads, tubes, biosensors, pressure transducers, dialysis probes, flow transducers, thermistors and movement sensors for example. In FIG. 2, a patient's cranium is indicated at 100, and a set of EEG leads are shown at 101 as an example of an input signal source. Leads 102 and 103 also attached to the patient's scalp indicate other input signal sources.

The input signals are filtered as necessary, amplified and analogue-to-digital converted where necessary, and optionally multiplexed together, as indicated by block 104, and passed to data buffer 105. Other input parameter data from other instruments for example or other data sources may optionally also be input to data buffer 105.

The digitised input signals data may also be compressed and stored. Data compression may involve averaging or time-to-frequency domain conversion.

Standard computer-compatible data storage devices with a standard system for file naming and configuration are utilised. The system is capable of carrying out data reduction, feature extraction, or compression, of incoming signals of a variety of types. For example, EEG spectra and ECG waveform data are averaged. In particular, conversion of an EEG, for example, from the time domain to the frequency domain prior to storage can result in a substantial reduction of data, as does recording of its mean intensity. Data reduction is a common consequence of median and/or other forms of filtering.

At block 107 the expert system software embodying expert analytical rules represented by block 108 is applied to the current and the stored data for the patient being monitored. The expert system rules are developed from accumulated experimental and clinical experience, as described subsequently. The system continuously samples and analyses each of the input channels, at a rate appropriate to the input channel. The expert software system may be considered as a number of brain rescue task instruments indicating various parameters from the input data. In either case the software system is configured to display at least some of the parameters being monitored, either selected by the expert software system as the most appropriate to display to the clinician for the particular patient case, or a combination of parameters which is override selected by the clinician. The parameters which are normally displayed in the foreground for the particular patient case are those that together increase the ability to predict the outcome, or identify the phase of injury, or guide the selection and/or the application of a therapy to the patient. The software continues to monitor the non-displayed parameters in background and if any of these is considered by the expert software system to be such as to indicate a deterioration of the brain state of the patient, the software causes the previously background parameters to be displayed, by a pop up window showing the parameter value graphically for example, or causes a warning to be given to the user in some other way via an appearing icon or similar, optionally accompanied by an audible alarm if appropriate.

FIG. 2 also comprises a dataflow diagram and illustrates that digital signals are fed continuously into input data buffer 105, subsequently the bulk of the data flow is through the signal analytical modules 106, and then through the expert brain rescue task modules 107, and to the display, or data storage device(s). The signal analytical modules perform artefact rejection, signal processing and analysis, and data reduction. The expert brain rescue task modules then select information from these modules and process the information to aid specific brain rescue tasks. The brain rescue task modules select the pertinent biophysical measures to display and set the normal and pathological display ranges and data display modes and display scales.

For the foreground parameters the display normally shows the most recent period of data collection, and highlighted on the display, for each biochemical or biophysical parameter, are any points where there is at least a suspicion of pathophysiologic levels, or the optimal range for the biochemical or biophysical parameter that can influence outcome. For example, a line or series of points graphically illustrating a monitored parameter can be displayed in green where the corresponding parameter is clearly within a normal range, or in yellow, and then red for values that the expert system predicts to be unsafe or dangerous. A monochrome display may use brighter or flashing lines or points. Display scales may be non-linear particularly in the display of spectra or where logarithmic displays are already accepted. The display may also be non-linear in the time axis if this can be portrayed without risking confusion. Alternatively different windows on a screen may display short-term events or long-term events respectively.

User interaction with and control of the system in the preferred form system is via a touch sensitive screen but may alternatively be via a touch panel or keypad 109 (see FIG. 2), on the front face of the preferred form instrument for example, a keyboard and/or a mouse, a separate hand held infra-red unit, or other convenient form of input device.

The unit may include a printer port 113 or a built-in printer, or a network interface.

Both short-term events (of the order of 4 seconds) and long-term events (of the order of hours or days) are resolved, evaluated, and displayed. The sampling rates used are capable of resolving brief events and also of separating a real, brief event from an artefactual single or series of false values, and the unit is capable of storing and recalling of any or all records over a period of for example 3 days or more. Such artefacts and interference from the input parameters may be minimised via one or more hardware or software filters, and/or via expert rules in the software applied at the signal processing stage indicated by block 106 capable of rejecting events not in accordance with the time scale of the signal being recorded. For example, EEG recordings become unreliable with increased electrode impedance and/or amplifier saturation and/or presence of movement artefact, and one sign of movement artefact is rapid fluctuations in the shape of the waveform. A preferred software filter is a median filter which tends to reject extreme values such as those resulting from a switching transient coupled to the body.

Figure 5:
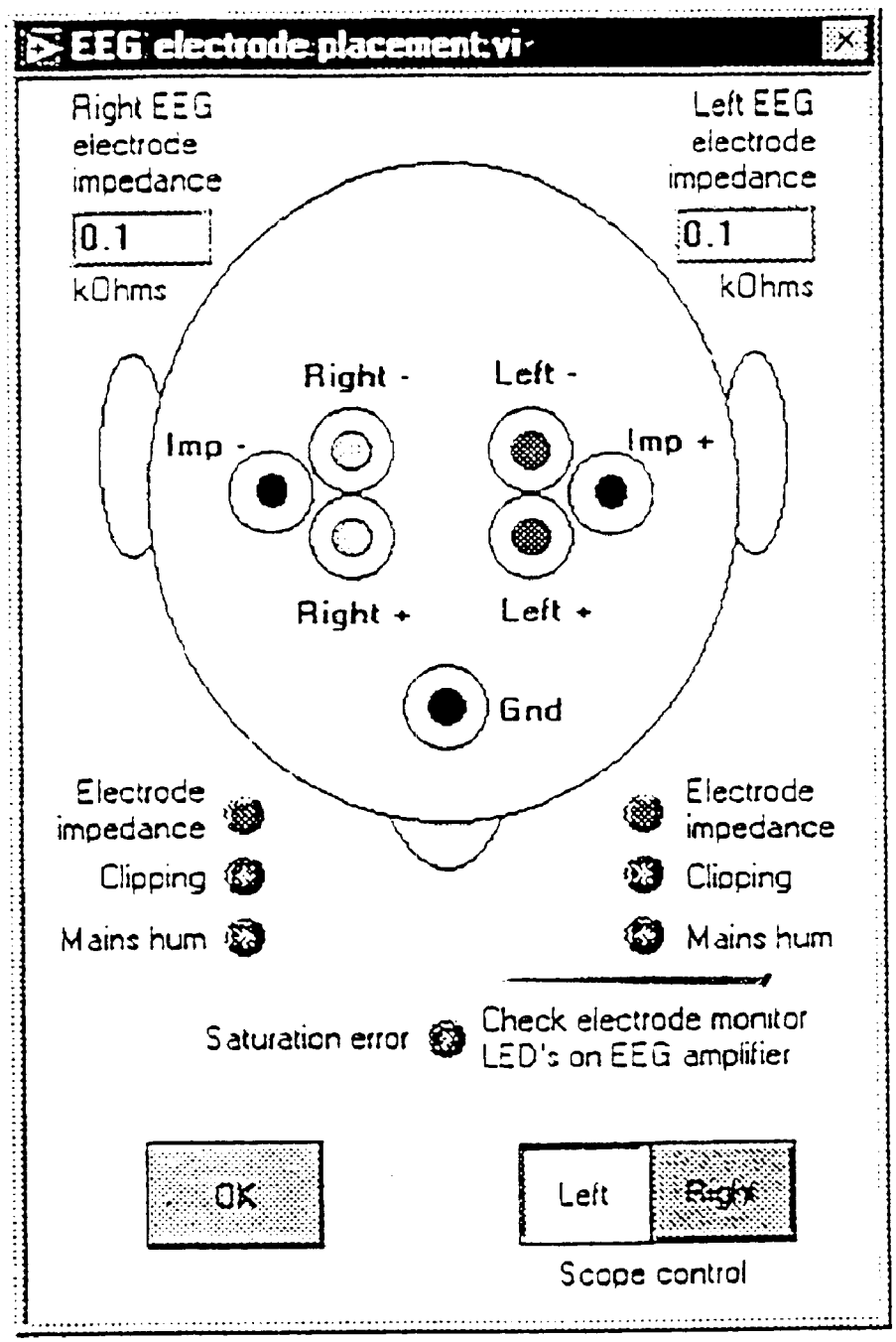
FIG. 5 shows preferred EEG electrode placement for use with the preferred form brain rescue monitor.

The system is so far as possible is capable of assessing the effectiveness of sensor connections and informing the user of any signal channels that appear to be incorrect. The system monitors each signal line in order to confirm that each channel continues to provide reliable results because (for example) attached electrodes can be detached or lose effectiveness in other ways. In the event of a problem the corresponding data is disregarded and a warning message is generated. FIG. 5 shows a display screen of the preferred form brain rescue monitor which illustrates the preferred EEG electrode placement, and which may also indicate to the user any detached or ineffective electrode. The system will also calibrate itself, as far as possible, so that readings are quantitative. This means that they have a greater reliability and significance to an expert system.

Figure 3:
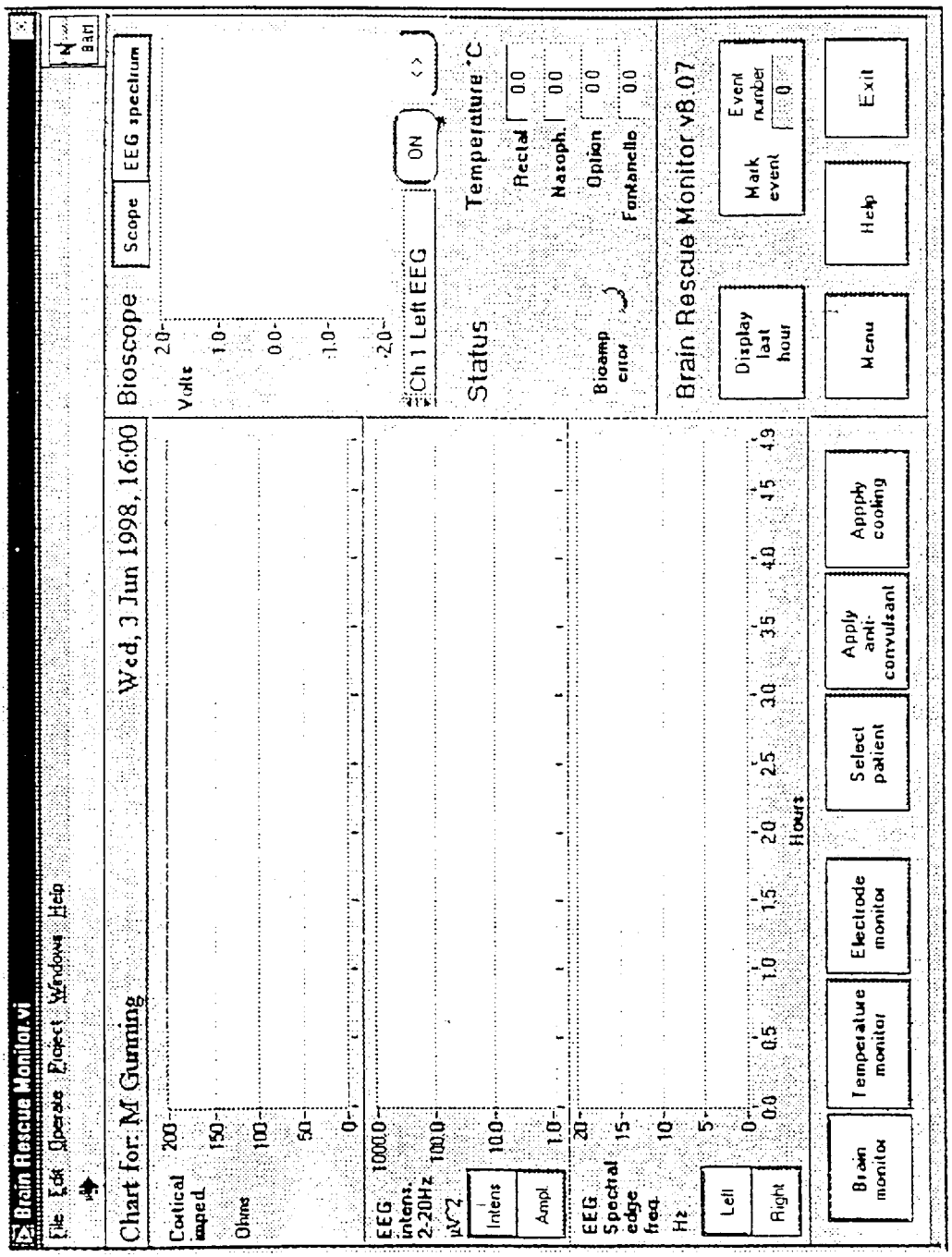
FIGS. 3 and 4 show screen displays of the preferred form brain rescue monitor.

FIG. 3 shows a screen display of the preferred form brain rescue monitor. Information relevant to specific brain rescue tasks or for the monitoring or management of brain injuries is displayed on the screen (see text and observational data). The information to be displayed is selected by the user via the menus such as the brain rescue task menu displayed along the bottom left of the screen. In this example time trend information describing pathophysiologic, cytotoxic and physiologic processes are displayed graphically in the upper left region. Incoming signals are monitored in the upper right region and current patient status information is displayed in the panel on the right. The user may also mark events, access the help information or alter the settings of the machine via the menus in the lower right corner of the screen. The user also can alter the information displayed within specific regions by accessing the associated menus.

Figure 4:
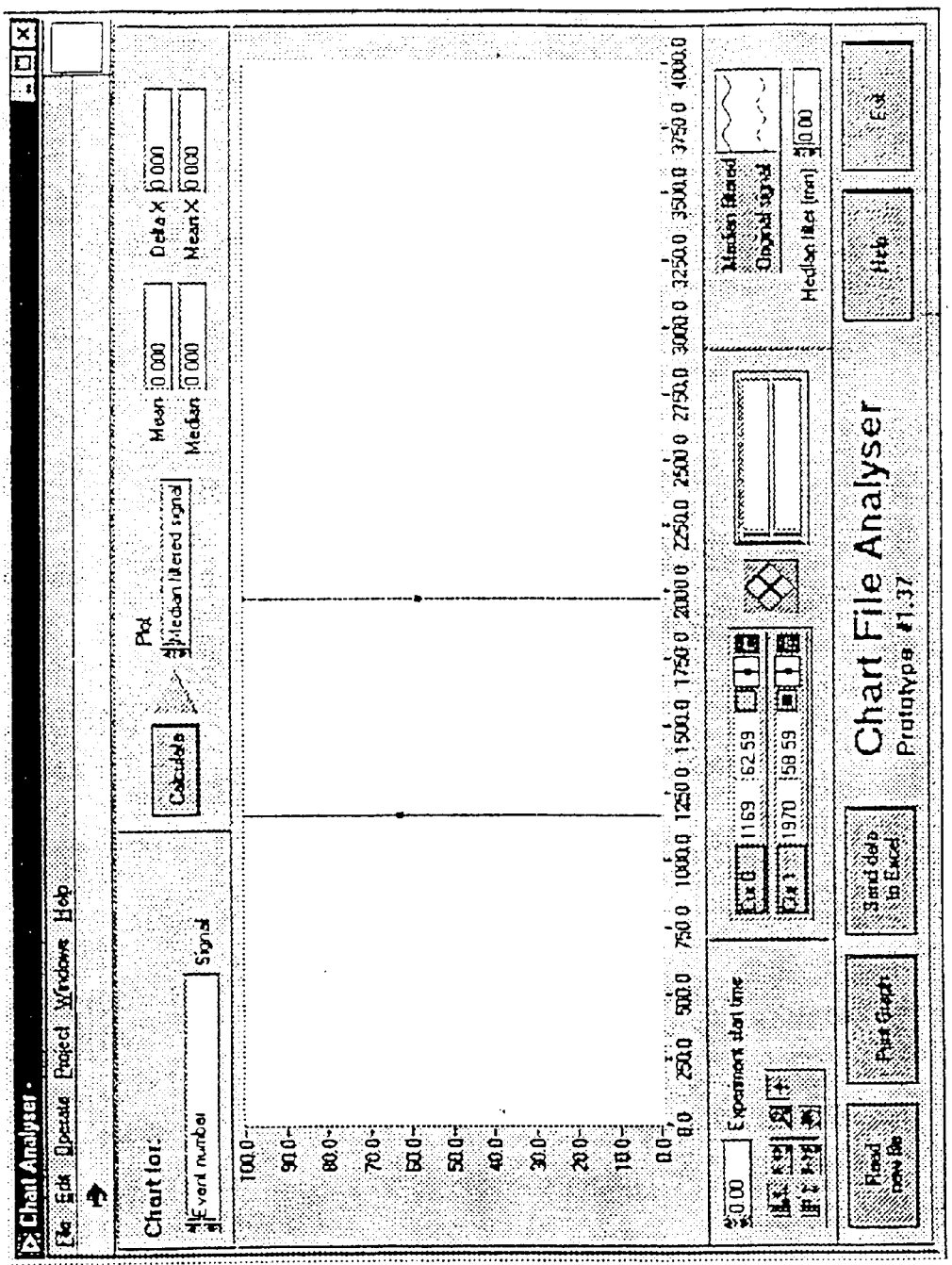

FIG. 4 shows another screen display of the preferred form brain rescue monitor for the evaluation and analysis of historical and/or data remotely recorded by the brain rescue monitor. The user can select the information to be displayed, zoom, scroll, take measurements, filter, process or print or extract information as required via the menus.

More generally in relation to system alarms, the expert system may give a warning to the user when an alarm limit for any parameter is exceeded, by an alarm tone graded according to severity, a visual alarm message colour coded according to severity or by flashing a visual alarm message for a particular parameter, for example. Alarms can be indefinitely suspended for 1, 2 or 3 minutes, after which the alarm will automatically reactivate. In the preferred form unit to prevent unwanted alarms, the parameters which will trigger an alarm may be entered by the clinician. Alarms may be graded and prioritised for example as red alarms to indicate a critical situation occurring; yellow alarms to alert clinicians when alarm limits are exceeded; and technical alarms which are triggered by signal quality noise and problems, and equipment malfunction.

Optionally the system may make available expert advice having an inbuilt ability to predict outcome and/or to identify the pathological processes taking place through an advisor/help system. Some of the rules by means of which this can be set up are evident from the following observational evidence, and an expert system for indicating an appropriate response may be based on a set of rules, and/or on fuzzy logic (such as numerical weighting of observations), and/or neural networks, and/or analytical models, a combination of those, or those plus additional computational abilities. The system may also make available representative examples of pathophysiologic reactions which can be called up by a user contemplating the case under study. Representative case studies may assist users to interpret findings, and may assist expert system in making its findings.

The software system applies an expert system of rules or expert analytical models to the signals so that the stage of evolution of head injury can be identified; the trends in the evolution of the case are recognised; cytotoxic processes can be identified; a likely outcome can be determined; and therapy can be recommended, particularly if some treatable and dangerous condition such as epileptiform activity (which may not result in motor activity) is identified.

The parameters which can be usefully monitored in any case may be deducted from the observational evidence disclosed below but specific examples of brain rescue tasks and the corresponding pathophysiologic, cytotoxic and physiologic responses that can be usefully monitored include:

Patient selection for rescue therapy: eg selection of infants who have suffered an asphyxial episode for neuronal rescue therapy. The biophysical signals monitored includes measures of some of the following pathophysiologic and cytotoxic processes:

Comprised cortical electrical activity eg loss of EEG intensity and/or amplitude and/or frequency.

Presence of cardiovascular injury eg presence of hypotension and/or changes within the ST segment of the electrocardiogram.

Presence of cerebral mitochondrial dysfunction or altered metabolism: eg increased cerebral lactate production and/or reduced cerebral oxygen consumption.

Altered cerebrovascular tone eg increased cerebral blood flow and/or blood volume or decreased cerebral blood flow and/or blood volume.

Patient rejection criteria can include some of the following:

Presence of normal EEG activity eg EEG intentsity and/or amplitude and/or frequency within normal range.

Evidence of persistent cytotoxic edema eg persistently elevated brain tissue impedance.

Evidence of brain death eg persistent loss of brain blood flow.

Postasphyxial seizure detection and management: eg for identifying and guiding therapy of those suffering from postasphyxial seizures. Therapy may be either anticonvulsant or antiexcitotoxic agents. The biophysical signals monitored includes measures of some of the following pathophysiologic and cytotoxic processes:

Cortical seizure activity eg presence of seizure activity on the EEG signal.

Level of background EEG activity eg EEG intensity and/or amplitude and/or frequency.

Spatial distribution of some of above EEG parameters eg derived from EEG signals recorded at multiple sites.

Cytotoxic edema eg presence of increased brain tissue impedance.

Excitotoxic activity eg presence of increased glutamate in the brain cerebrospinal fluid and/or extracellular fluid.

Compromised cerebral metabolism eg reduced cerebral oxygen consumption and/or increased cerebral lactate production and/or lactate levels in cerebrospinal fluid.

Presence of hyperaemia eg increased cerebral blood flow.

Synchronous increases in blood pressure and/or heart rate, and/or blood flow and/or muscle activity.

Increases in core and/or cerebral temperature.

Monitoring of electrophysiologic signal validity: Signals to be monitored may include some of the following:

Range of electrode impedance.

Level of mains hum.

Presence of amplifier clipping.

Presence of input amplifier saturation.

Level of movement artefact.

Application of therapeutic hypothermia: The biophysical signals monitored includes measures of some of the following physiologic and pathophysiologic processes:

Core, cerebral and related temperatures:
These temperatures are referred against an optimal temperature range that depends on the protocol for example: term infants may be cooled to a core temperature of about 35° C. and adults 33° C.

Duration of cooling for example about 12–72 h post injury.

Rate of progressive rewarming eg about 1° C. per hour.

Heat transfer device(s) temperature status and heat flux(es).

Metabolic or cardiovascular compromise eg systemic lactate levels and/or hypotension.

Pathophysiologic or cytotoxic processes influenced by the hypothermia such as cytotoxia edema, vasogenic edema, excitotoxicity, or cerebral lactate production.

Maintenance of optimal status to minimise delayed neoronal injury: The biophysical signals monitored includes measures of the levels of some of the following physiologic and pathophysiologic processes:

Glucose levels eg serum levels and/or cerebrospinal fluid levels.

Core and/or cerebral temperature.

Blood pressure eg above a minimal (hypotensive) level.

Cerebral oxygenation eg measured by near infrared spectroscopy.

Cerebral perfusion eg measured by ultrasonic methods.

Intracranial pressure eg measured by intracerebral pressure sensors.

Presence of seizures eg detected on the EEG signals.

Observational Evidence

The following comprises observations for particular biophysical parameters. By appropriate weighing of each parameter an expert system for many cases can be produced capable of correctly assessing the likely patient outcome, of indicating the need for specific treatment (such as antiseizure treatment, seizures seem to immediately precede secondary neuronal death), and of indicating the progress. The brain rescue monitor enables the amount of data assessed to exceed that which an individual clinician can adequately comprehend.

Cerebral electrical activity—EEG: Referring to FIGS. 10, 11, 12 and 18, prolonged depression of EEG activity after injury is predictive of neuronal loss. Hypothermia or rescue therapies should be initiated in the depression phase, and a depressed EEG is associated with increased susceptibility to further injuries. Recovery of normal activity is associated with good outcome.

Figure 10:
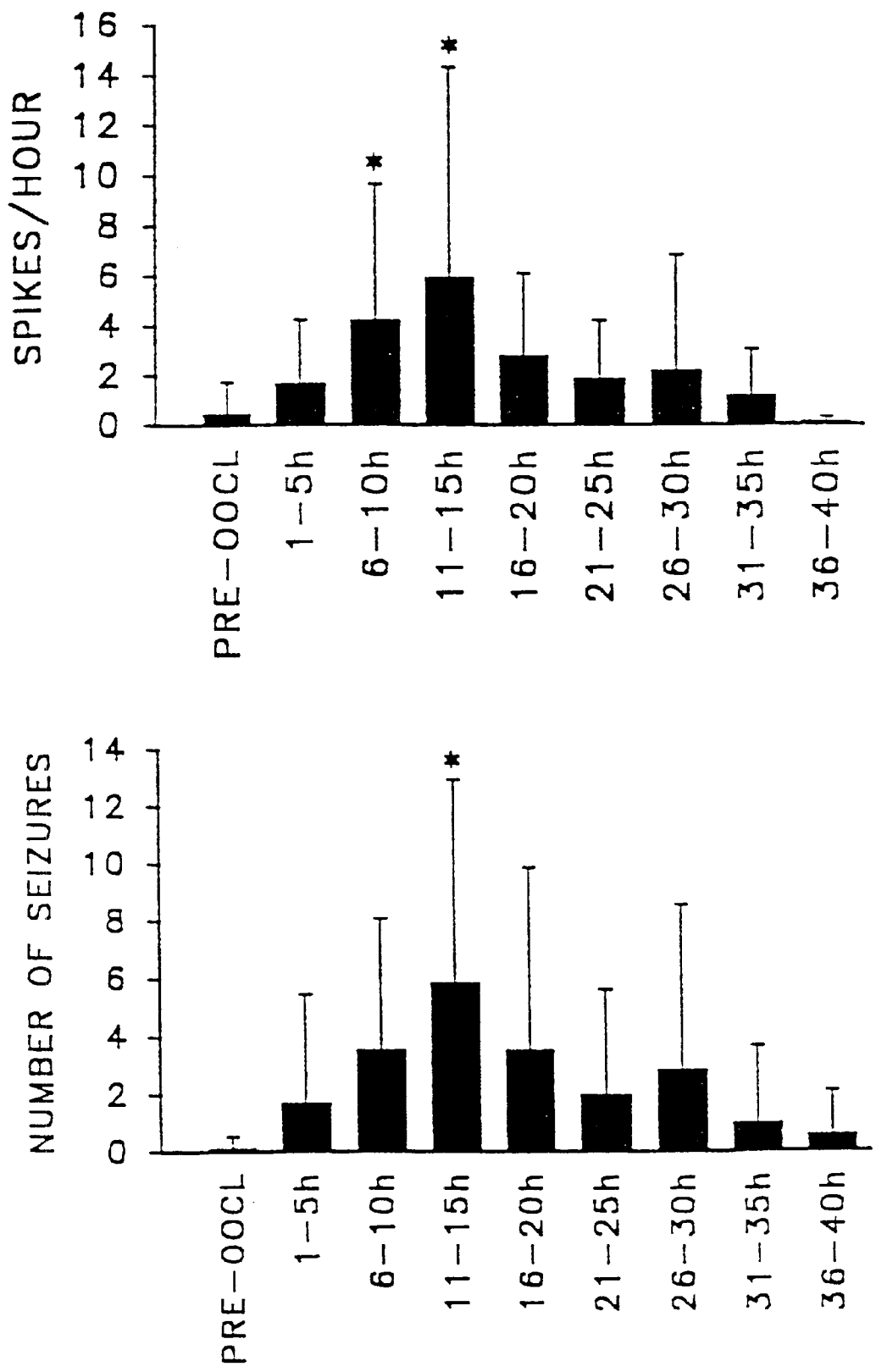
Figure 11:
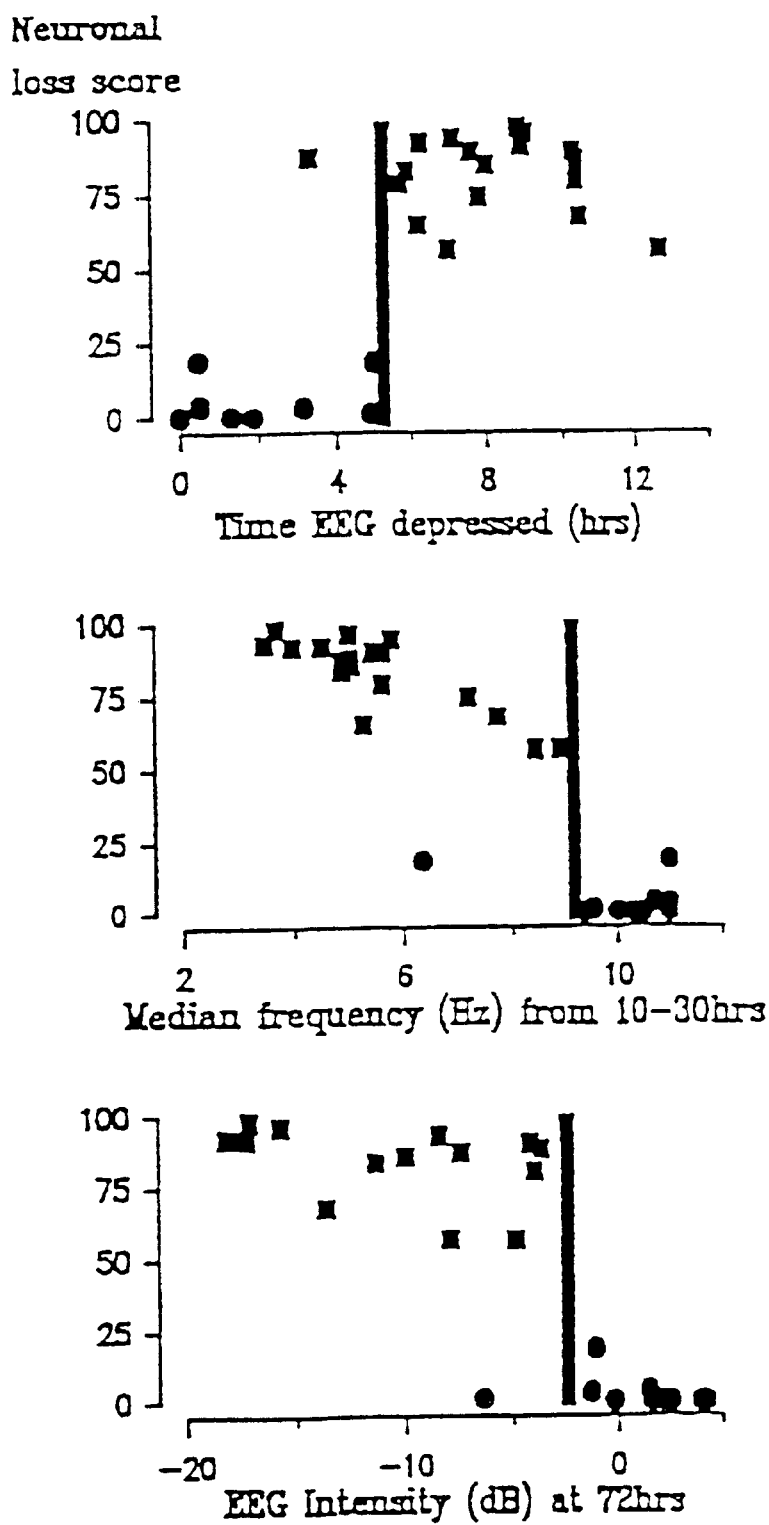
FIGS. 11(a)–(c) illustrate relationships between EEG parameters and outcome, FIGS. 12(a) and (b) are tables which correlate blood pressure and other factors, vs neuronal outcome, FIG. 13 graphically relates the duration of ischemia to neuronal loss in specific areas of the brain, FIG. 14 graphically illustrates cytotoxic activity as levels of citrulline (a marker of nitric oxide activity) and as cortical impedance (CT) vs time, FIG. 15 graphically shows by example the effect of growth factor (rhIGF-1) rescue therapy on pathophysiology, FIG. 16 diagrammatically shows the phases of brain injury.

Patient seizure activity (detected via EEG electrodes): Referring to FIG. 10 and FIGS. 8, 14 and 18 linking EEG activity to impedance, seizure activity after injury is predictive of neuronal loss, prolonged cortical seizure activity is predictive of cortical infarction, seizure activity and/or rise in impedance is associated with excitotoxicity (see later for details of impedance), seizure activity develops concomitantly with the secondary rise in impedance, seizure activity occurring with lowering of frequency predicts neuronal loss, synchronous increases EMG activity or rises in blood pressure or cerebral impedance are associated with severe seizures, Seizure activity is suppressed during effective therapy with antiexcitotoxic or anticonvulsant (FIG. 17) agents, and EEG depression before the onset of spike and/or seizure activity is associated with poor outcome (FIGS. 11, 12(*b*) and 18). Intermittent seizure activity superimposed on normal EEG activity is associated with striatal injury (FIG. 10).

Figure 17:
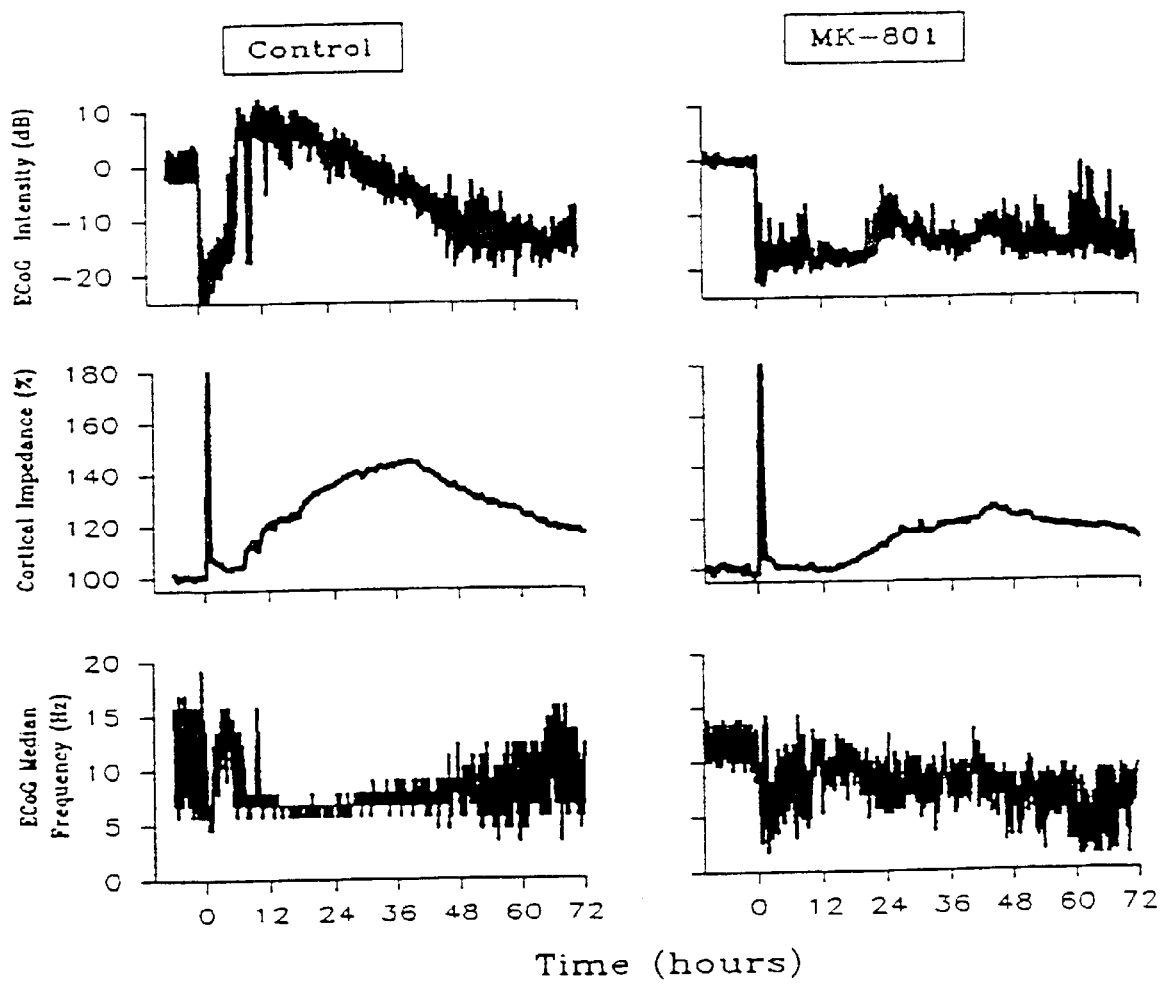
FIGS. 17(a) to (c) graphically show an example of the effect of MK801, a NMDA antagonist, on seizures and outcome.

Patient spike activity (detected via EEG electrodes): Referring to FIGS. 10 and 17, spike activity (bursts of rapid waves) is predictive of neuronal loss, spike activity often precedes seizure activity, and spike activity after depressed EEG and/or rise in cerebral impedance is predictive of neuronal loss. Spike activity superimposed on normal EEG activity is associated with striatal injury, and it is useful for the system to raise an immediate alarm if spike injury is detected (FIG. 10). The effect of administering MK801 is illustrated in FIG. 17; where the cortical impedance trace shows a much reduced rise.

Cerebral impedance (detected via EEG electrodes): Referring to FIGS. 8, 14, 15 and 18, rising impedance is associated with tissue energy failure, cytotoxic edema, rising impedance and EEG depression is associated with tissue energy failure, rising impedance and ischemia is associated with tissue energy failure, a reversible increase in impedance predicts delayed damage, and an acute rise in impedance predicts increased susceptibility to further injuries. (Ganglioside therapy can be used to counteract against increased susceptibility.) Irreversible acute risk in impedance predicts infarction, increased impedance is associated with accumulation of excitotoxins (FIGS. 8, 14, 17), prolonged secondary rise in impedance is associated with infarction and edema, gradually rising impedance and seizure activity is associated with the development of an infarct, prolonged large rise in impedance and loss of electrical activity is associated with brain death, a rise in impedance associated with the secondary phase of injury is associated with neuronal loss, falling impedance after a prolonged rise is associated with infarction, falling impedance and resolution of seizure activity or loss of EEG activity is associated with infarction, regional changes in impedance are associated with the location of injury, and cerebral impedance is influenced by temperature. Repetitive increases in impedance are associated with striatal injury. One example of alleviation of the signs of cerebral impedance changes is given in FIG. 15, where varying amounts of the growth factor rhIGF-1 (or vehicle alone) were given to ovine foetuses at about two hours after ischemia. There are a number of other possible treatments.

Figure 18:
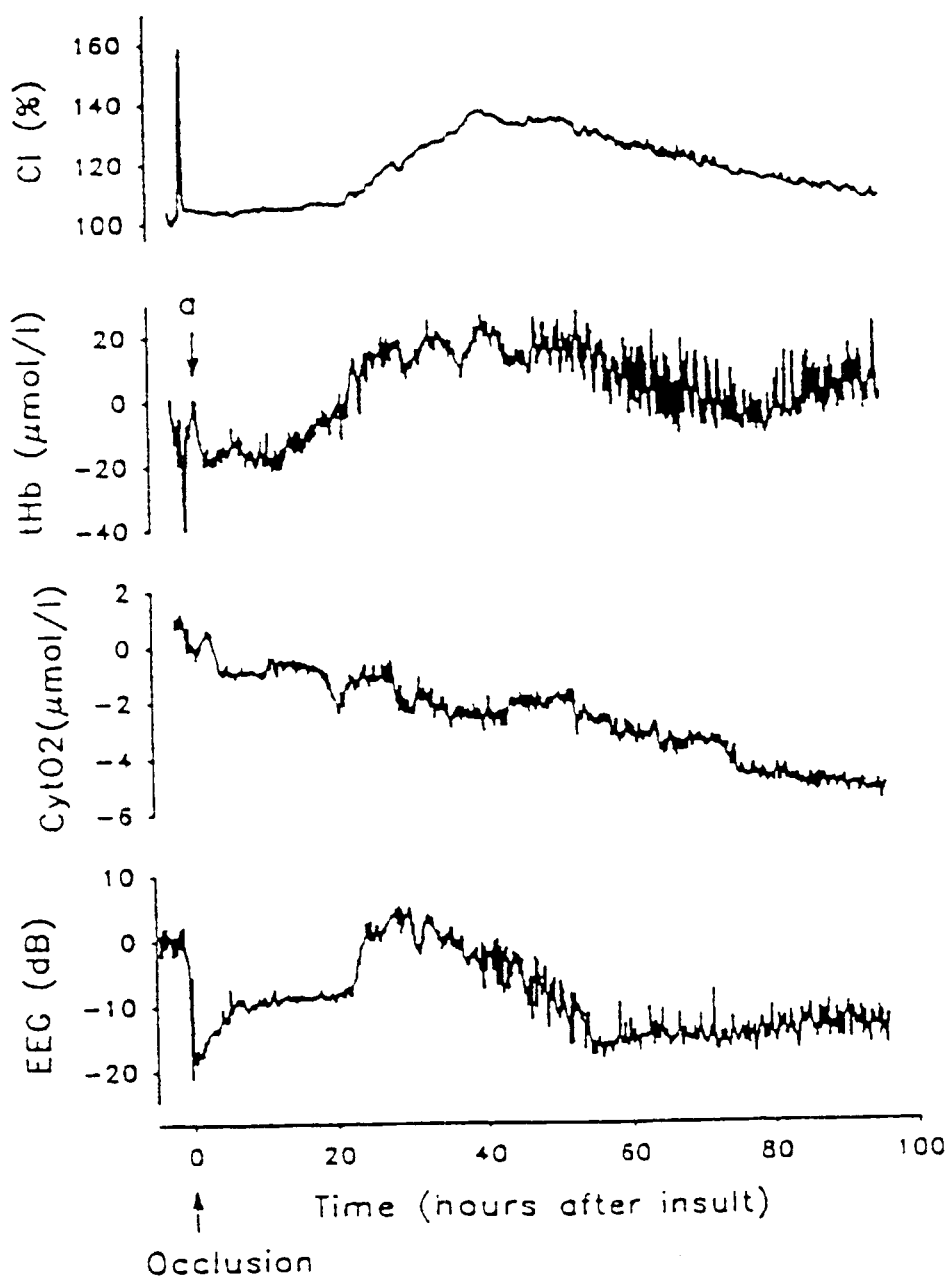
FIG. 18 shows a further set of curves relating cerebral impedance (CI), perfusion (tHb), cytochrome oxidase (CytO2), and EEG intensity, to time.
Figures 19, 20:
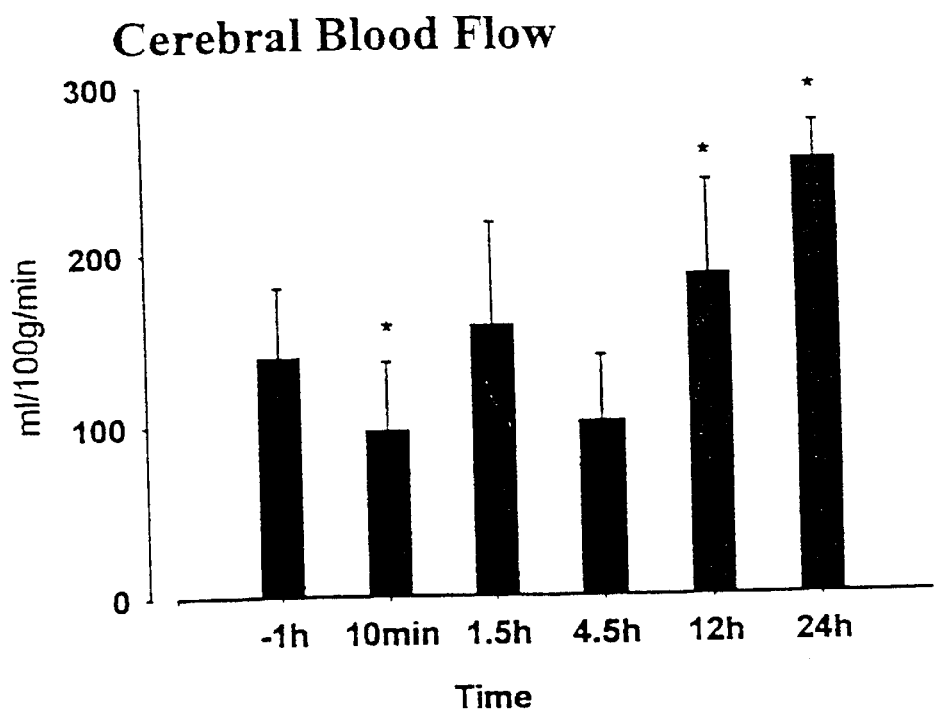
FIG. 19 is a table which correlates cortical neuronal loss versus perfusion, FIG. 20 graphically shows the time course of global cerebral blood flow following hypoxic-ischemic injury ($p<0.05$), FIGS. 21(a)–(d) graphically show the time course of changes in parietal cortex extracellular lactate, glucose, ECoG intensity and cortical impedance that occurs during and for 3 days following a 30 minute hypoxic-ischemic injury ($p<0.05$)

Cerebral hacmodynamic status: Referring to FIGS. 18 and 20, loss of cerebral oxygenation is associated with injury: The duration of primary hyperaemia (increased blood flow and/or blood volume) is predictive of poor outcome, the onset time of secondary hyperaemia is predictive of severity, secondary hyperaemia precedes edema and/or seizures, and hyperaemia increases during seizures and/or edema Episodes of venous desaturation are associated with poor outcome.

Cerebrovascular status: Referring to FIGS. 18, 19 and 20, impaired autoregulation is associated with poor outcome, and regional changes are predictive of outcome.

Cerebral blood flow: Referring to FIGS. 19 and 20, impaired cerebral blood flow is associated with injury, and increases in cerebral blood flow are associated with cerebral seizure activity and delayed injury. The degree of hypoperfusion during the immediate reperfusion period and an inverse relationship with the magnitude of delayed hyperperfusion are predictive of the severity of neuronal loss (FIG. 12*b*). Reactive hyperaemia occurs during the delayed phase of cell death after injury and may protect marginally viable tissue (FIGS. 18 and 20).

Figure 8:
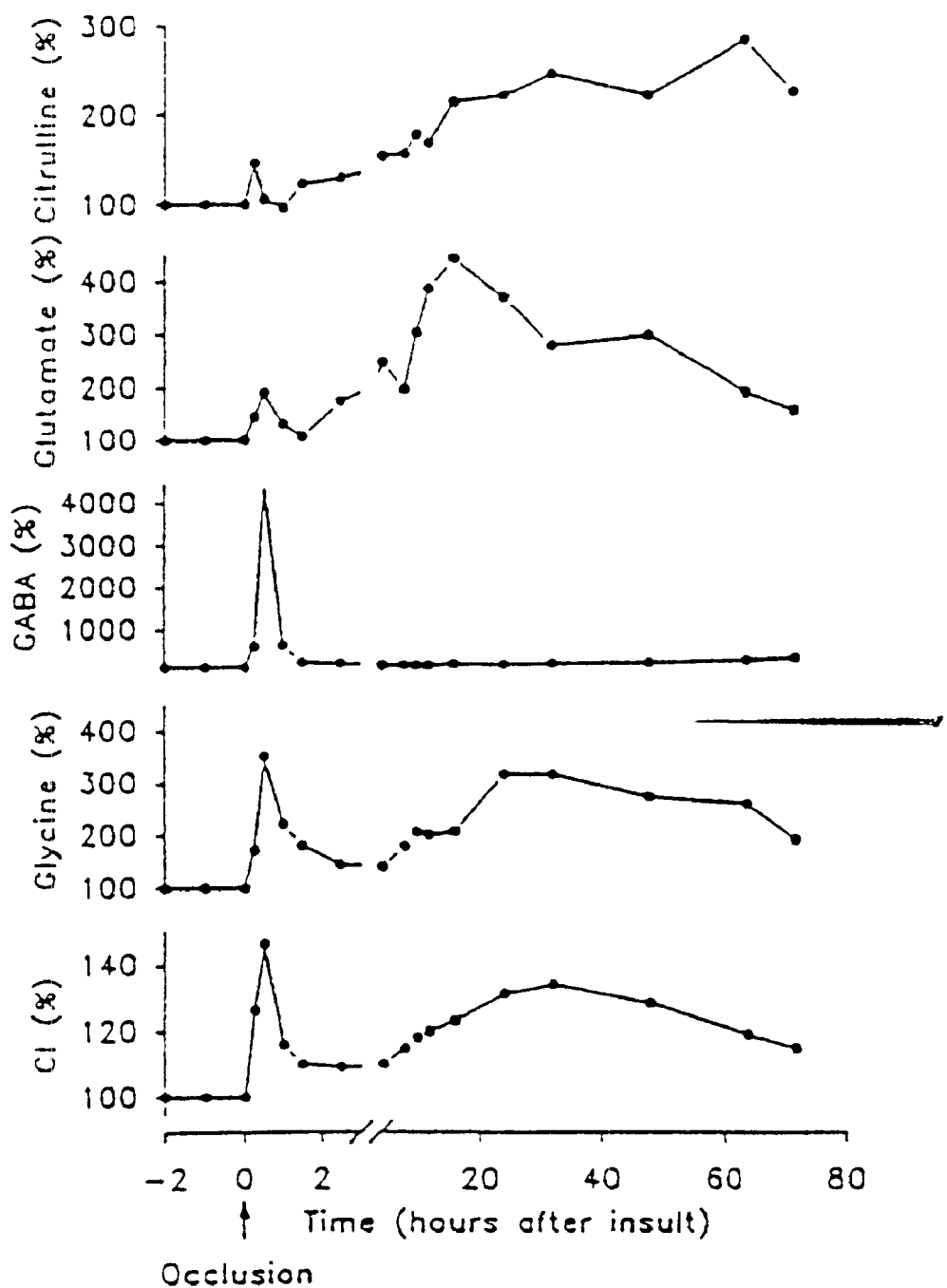
FIG. 8 graphically shows cytotoxic activity as sensed by microdialysis, against time, FIG. 9 graphically shows examples of the T/QRS ratio from an ECG after injury, FIGS. 10(a) and (b) graphically show seizure and spike activity after injury, overtime.
Figure 14:
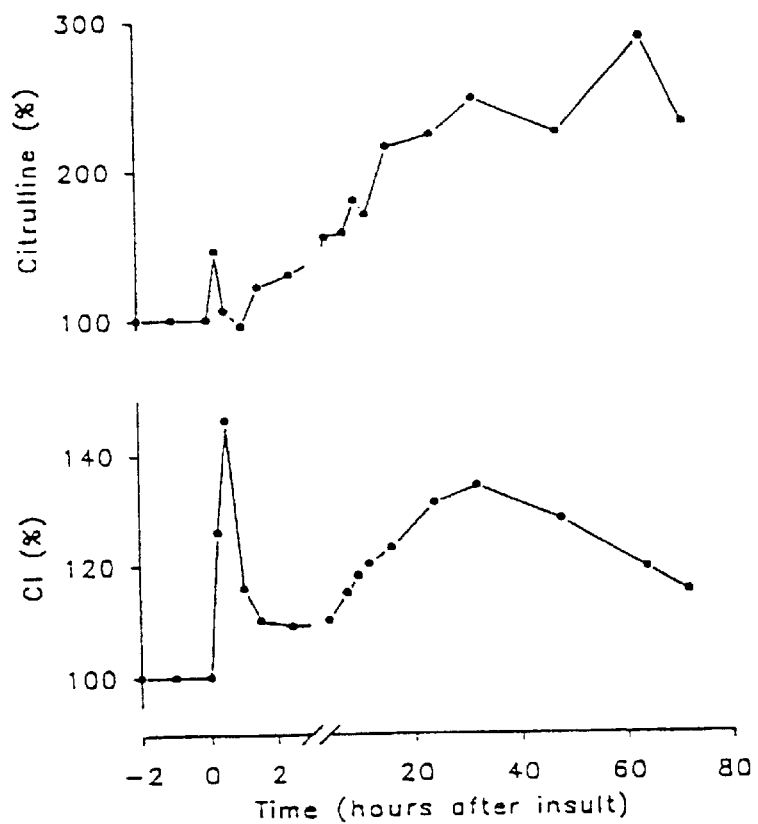
Figure 15:
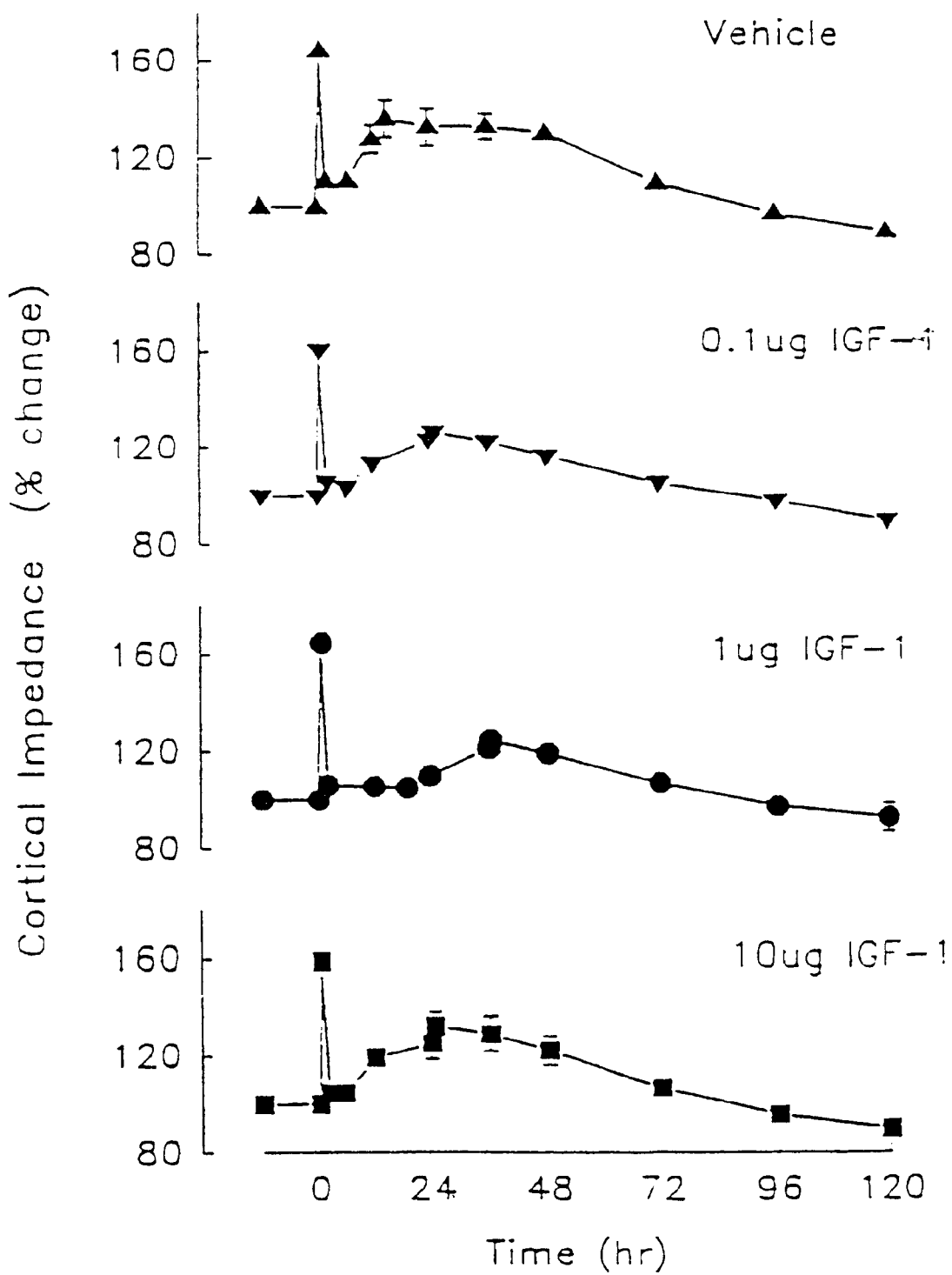
Figure 16:
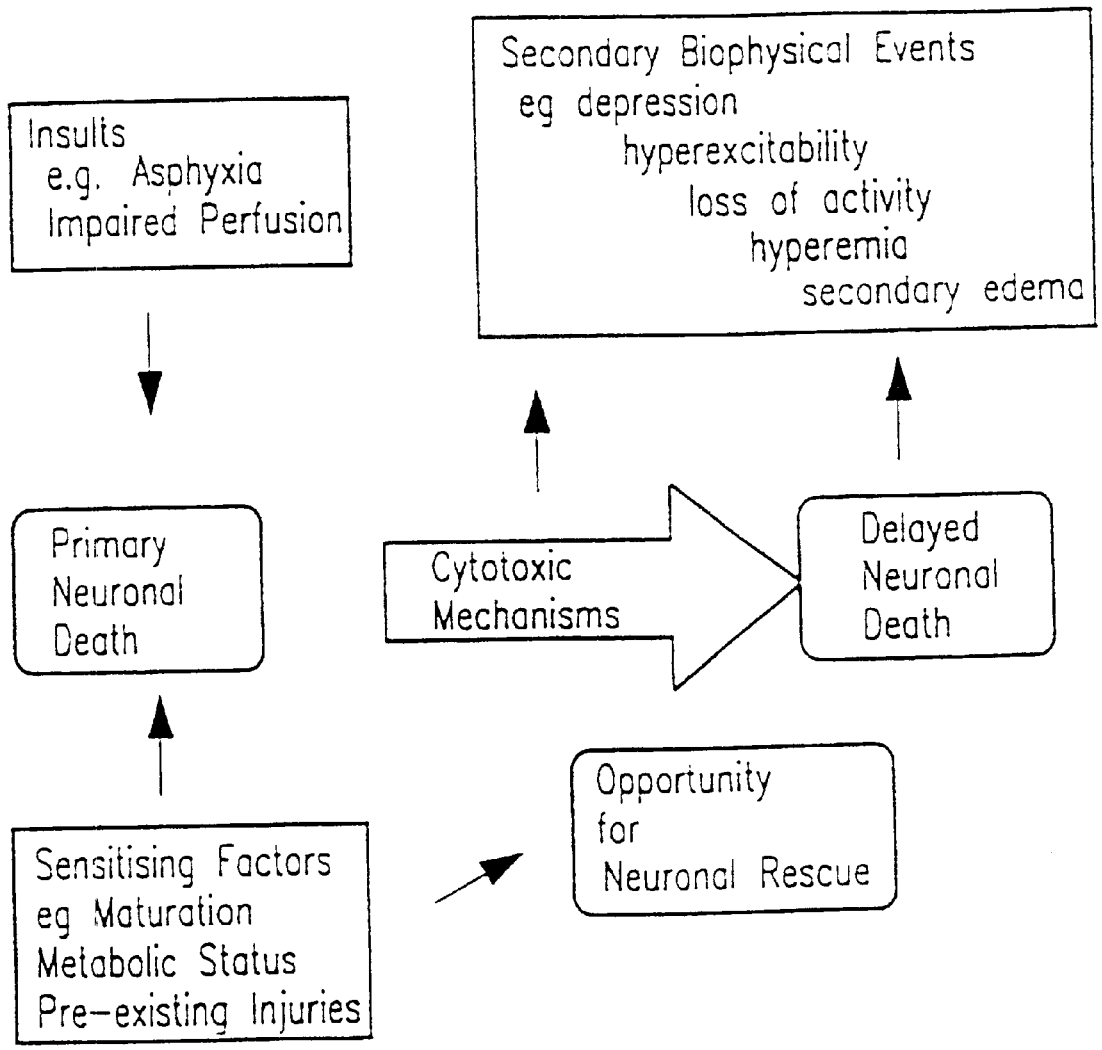

Cytotoxic activity: Referring to FIGS. 8 and 14, a rise in extracellular citrulline, a by product of nitric oxide, is associated with delayed injury. Excitotoxins, such as glutamate, accumulate during the later phases of injury (FIGS. 8 and 17). Increased levels of cytotoxins are associated with poor outcome.

Figure 21:
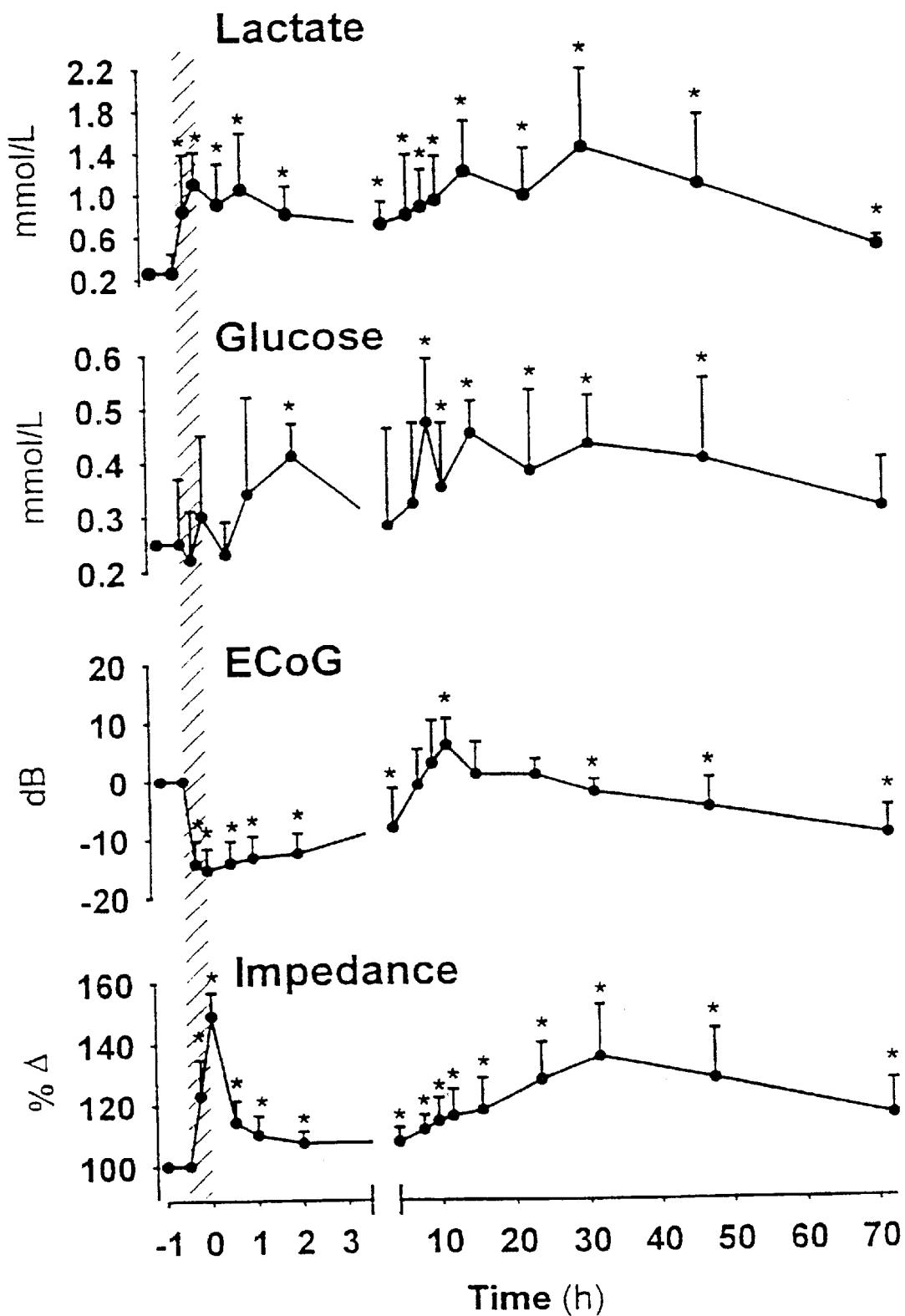

Lactate status: Referring to FIG. 21, Increased production of lactate, a marker for mitochondrial damage, is associated with the early phase of injury. Elevation in lactate levels are associated with the delayed phase of injury.

Glucose status: Referring to FIG. 21, an elevation in glucose is associated with the delayed phase of injury. Both hypoglycaemia and hyperglycaemia can worsen brain injury.

Figure 13:
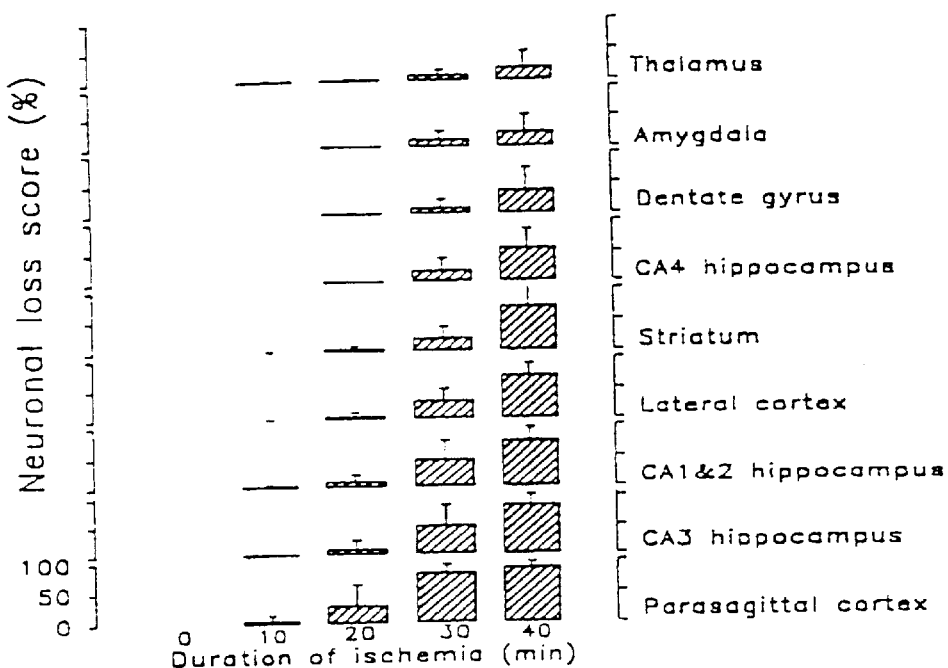

Spatial distribution: Referring to FIG. 13, spatial distributions of cerebral pathophysiologic processes are monitored because spatial changes are associated with the location of pathophysiologic processes eg changes in EEG can be used to localise changes.

Figure 9:
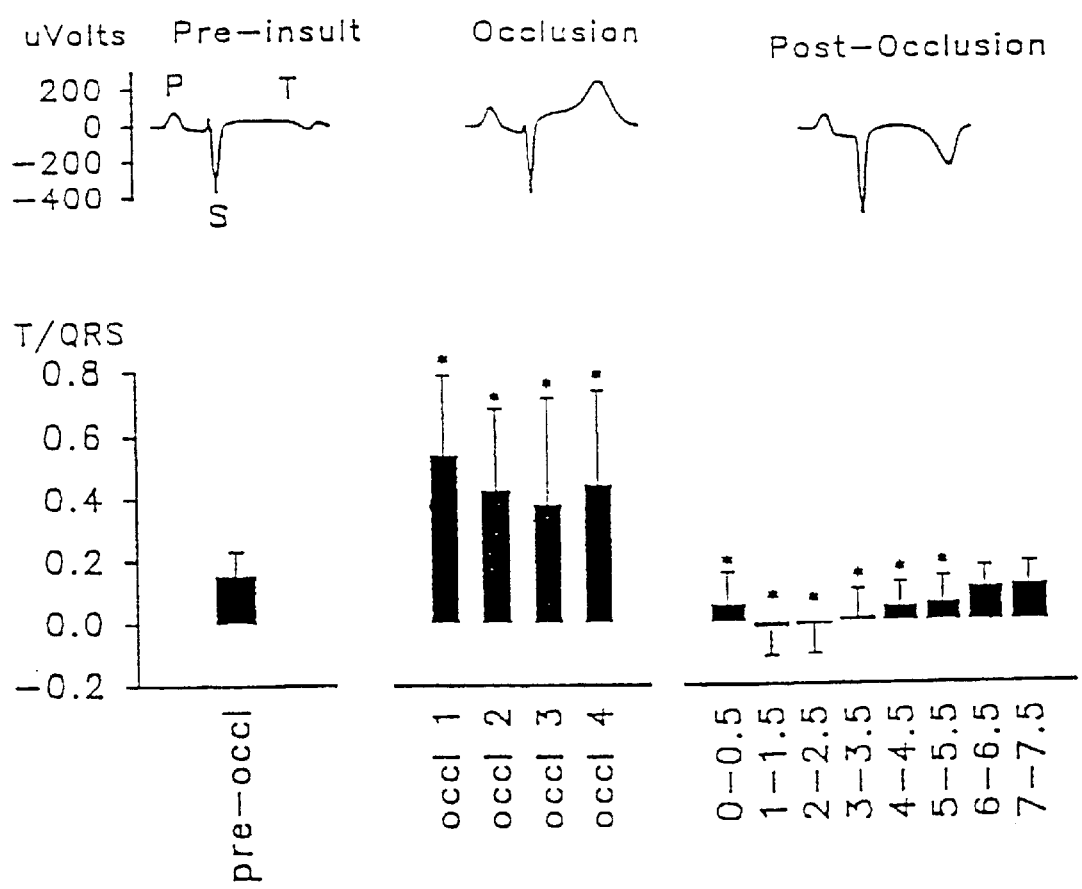

ECG: Referring to FIGS. 9 and 12, the occurrence of ST changes after asphyxia is predictive of neuronal loss, T wave changes after asphyxia is predictive of neuronal loss, and acute changes in T/QRS ratio are associated with cerebral injury.

Figure 6:
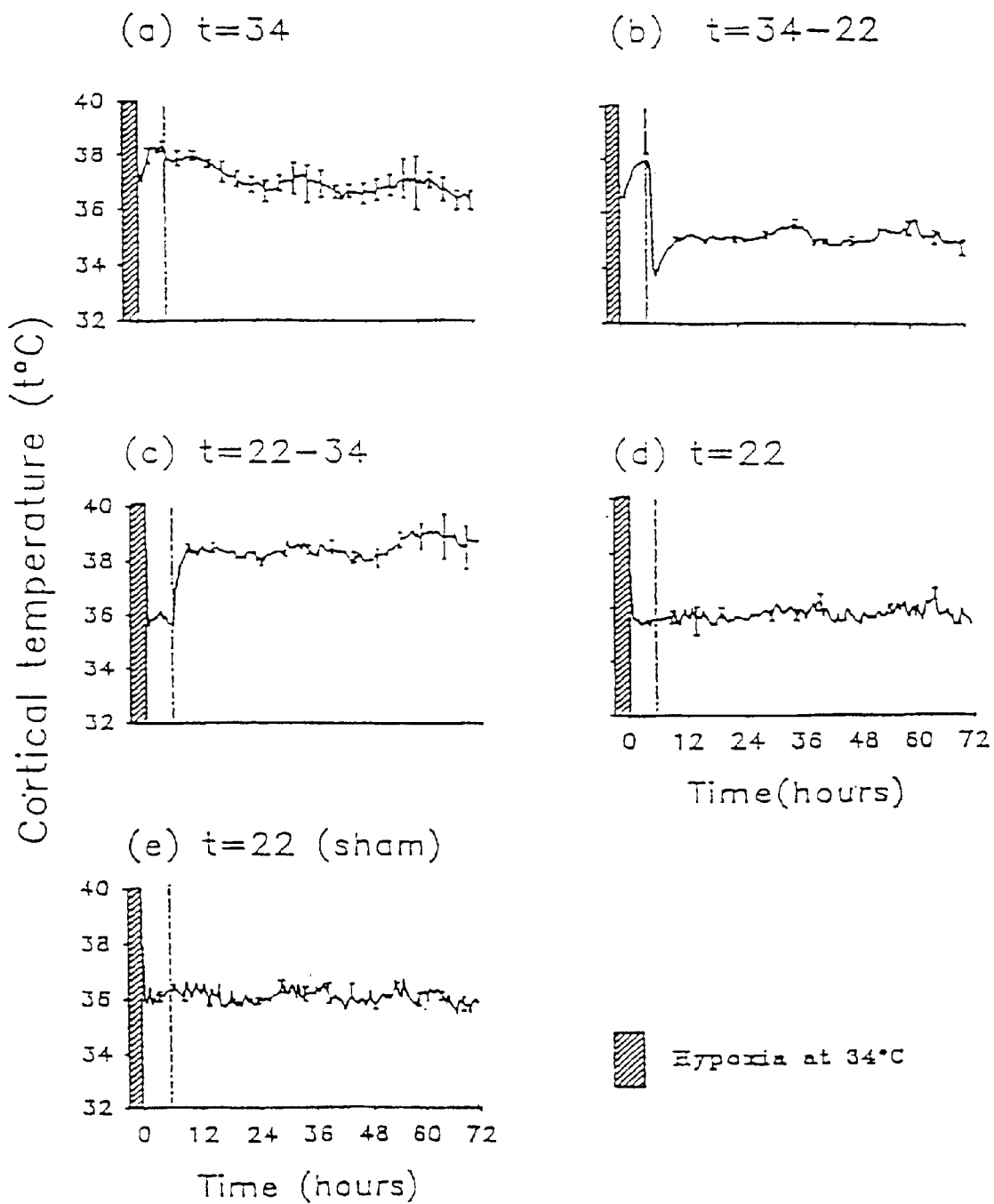
FIGS. 6(a) to (e) are graphs of a series of cortical temperature treatment profiles following hypoxia, FIGS. 7(a) to (e) graphically show examples of effects of long term temperature trends on outcome.

Temperature: Referring to FIGS. 6 and 7, preferably at least core, tympanic and scalp temperature are monitored. Hyperthermia exacerbates injury until cerebral function has fully recovered, while prolonged hypothermia suppresses neuronal death, scalp temperature influences cortical damage, and core temperature influences damage in deeper brain structures.

Arterial blood pressure is monitored, because hypertension increases the risk of injury: Referring to FIG. 12 cerebral perfusion pressure is monitored because low cerebral perfusion pressure increases risk of injury, secondary rise in impedance precedes brain swelling, and development of hyperaemia then rising impedance predicts brain swelling (FIG. 18).

The foregoing describes the invention including a preferred form thereof. Alterations and modifications as will be obvious to those skilled in the art are incorporated in the scope of the invention, as defined in the following claims.

What is claimed is:

1. A brain rescue instrument for use in identifying, monitoring, and guiding the application of brain therapies to patients at risk of secondary phase brain damage including delayed neuronal death, comprising:
    input means for acquiring a group of signals each indicative of a different biochemical or biophysical parameter of a patient and the behavior of which group of signals over time is indicative or predictive of developing secondary phase damage or a risk thereof, and
    computing means configured to continuously process and display to a user the acquired signals or information obtained therefrom on one or more time scales which show variations in the signals which are indicative or predictive of secondary phase brain damage or a risk of secondary phase damage.

2. A brain rescue instrument according to claim 1 wherein said group of signals includes an EEG signal or signals; a signal or signals indicative of brain edema; and a signal or signals indicative of one or more of core body temperature, cerebral temperature, and scalp or skin temperature.

3. A brain rescue instrument according to claim 2 wherein said EEG signals comprise signals from the both left and right hemispheres.

4. A brain rescue instrument according to claim 3 wherein said signal or signals indicative of brain edema include one or more of a signal indicative of brain tissue impedance, a signal indicative of cytotoxic edema, a signal indicative of vasogenic edema, a signal indicative of intracranial pressure, and a signal indicative of cerebral perfusion pressure.

5. A brain rescue instrument according to claim 3 useful in early prediction of risk of secondary damage, that can aid in the selection of patients for rescue therapy, wherein said group of signals includes an EEG signal or signals, and one or more of:
    an ECG signal,
    a signal indicative of cerebral lactate level(s),
    a signal indicative of cerebral oxygen consumption,
    a signal or signals obtained from the EEG signal(s) indicative of one or both of seizure and spike activity,
    a signal or signals indicative of brain edema,
    a signal indicative of cerebrovascular status,
    a signal indicative of cerebral haemodynamic status,
    a signal indicative of cerebral blood flow, and
    a signal indicative of blood pressure.

6. A brain rescue instrument according to claim 5 wherein said signal or signals indicative of brain edema include one or both of a signal indicative of brain tissue impedance and a signal indicative of cytotoxic edema.

7. A brain rescue instrument according to claim 5 arranged to highlight variations in at least some of the displayed signals or information which are indicative or predictive of secondary phase brain damage.

8. A brain rescue instrument according to claim 5 wherein said computing means is arranged to apply to at least some of the signals or information obtained therefrom expert analytical rules based on knowledge of the behavior of the signals over time during developing secondary phase brain damage, and to display to a user the signals or information obtained therefrom in a way which highlights variations identified by application of said expert analytical rules which are indicative or predictive of secondary phase brain damage or a risk of secondary phase damage.

9. A brain rescue instrument according to claim 3 useful in the detection and management of post insult seizures in patients, wherein said group of signals includes an EEG signal or signals; a signal or signals obtained from the EEG signal indicative of one or more of (i) one or both of cortical seizure and spike activity, (ii) the level and frequency of background EEG activity, and (iii) the spatial distribution of EEG derived signals; and a signal or signals indicative of one or more of:
    movement or muscle activity,
    heart rate,
    blood pressure,
    cerebral blood flow,
    cerebral haemodynamic status,
    brain edema,
    one or more of core body temperature, cerebral temperature, and scalp or skin temperature.

10. A brain rescue instrument according to claim 9 wherein said signal or signals indicative of brain edema include one or more of a signal indicative of brain tissue impedance and a signal indicative of cytotoxic edema.

11. A brain rescue instrument according to claim 9 arranged to highlight variations in at least some of the displayed signals or information which are indicative or predictive of secondary phase brain damage.

12. A brain rescue instrument according to claim 9 wherein said computing means is arranged to apply to at least some of the signals or information obtained therefrom expert analytical rules based on knowledge of the behavior of the signals over time during developing secondary phase brain damage, and to display to a user the signals or information obtained therefrom in a way which highlights variations identified by application of said expert analytical rules which are indicative or predictive of secondary phase brain damage or a risk of secondary phase damage.

13. A brain rescue instrument according to claim 3 useful in patient monitoring during hypothermia therapy, wherein said group of signals includes an EEG signal or signals; a signal or signals indicative of one or more core body temperature, cerebral temperature, and scalp or skin temperature; a signal indicative of heat transfer device function; and a signal or signals indicative of one or both of brain edema and cardiovascular compromise.

14. A brain rescue instrument according to claim 13 wherein said signal or signals indicative of brain edema include one or more of a signal indicative of brain tissue impedance, a signal indicative of cytotoxic edema, a signal indicative of vasogenic edema, a signal indicative of intracranial pressure, and a signal indicative of cerebral perfusion pressure.

15. A brain rescue instrument according to claim 13 wherein said signal or signals indicative of cardiovascular compromise include one or more of an ECG signal, a signal indicative of blood pressure, and a signal indicative of systemic lactate level(s).

16. A brain rescue instrument according to claim 13 arranged to highlight variations in at least some of the displayed signals or information which are indicative or predictive of secondary phase brain damage.

17. A brain rescue instrument according to claim 13 wherein said computing means is arranged to apply to at least some of the signals or information obtained therefrom expert analytical rules based on knowledge of the behavior of the signals over time during developing secondary phase brain damage, and to display to a user the signals or information obtained therefrom in a way which highlights variations identified by application of said expert analytical rules which are indicative or predictive of secondary phase brain damage or a risk of secondary phase damage.

18. A brain rescue instrument according to claim 3 useful in monitoring the brain status of patients for signs or secondary phase damage or a risk thereof wherein said group of signals includes an EEG signal or signal(s); a signal or signals obtained from the EEG signal or signals indicative of one or both of seizure and spike activity; a signal or signals indicative of one or more of core body temperature, cerebral temperature, and scalp or skin temperature; a signal indicative of brain edema; and a signal indicative of one or more of:
 cerebral oxygenation,
 blood pressure,
 cerebral blood flow,
 systemic glucose level(s),
 cerebral lactate level(s),
 cerebral glucose level(s), and
 cytotoxic edema.

19. A brain rescue instrument according to claim 18 wherein said signal or signals indicative of brain edema include one or more of a signal indicative of brain tissue impedance, a signal indicative of cytotoxic edema, a signal indicative of vasogenic edema, a signal indicative of intracranial pressure, and a signal indicative of cerebral perfusion pressure.

20. A brain rescue instrument according to claim 18 useful in monitoring the status of the evolving or secondary phases or neural injury of patients wherein said group of signals includes an EEG signal or signals; one or more signals obtained from the EEG signal or signals indicative of one or both of seizure and spike activity; a signal indicative of brain edema; and a signal indicative of one or more of:
 cerebral oxygenation,
 cerebral blood flow,
 cerebral haemodynamic status,
 cerebrovascular status,
 cerebral lactate level(s),
 cytotoxic edema,
 cerebral glucose level(s), and
 excitotoxic activity.

21. A brain rescue instrument according to claim 20 wherein said signal or signals indicative of brain edema include one or more of a signal indicative of brain tissue impedance, a signal indicative of cytotoxic edema, a signal indicative of vasogenic edema, a signal indicative of intracranial pressure, and a signal indicative of cerebral perfusion pressure.

22. A brain rescue instrument according to claim 18 useful in monitoring to predict risk of secondary phase damage to assist with minimization of delayed damage wherein said group of signals includes an EEG signal or signals; one or more signals obtained from the EEG signal or signals indicative of one or both of seizure and spike activity; a signal indicative of one or more of core body temperature, cerebral temperature, and scalp or skin temperature; a signal indicative of brain edema; and a signal or signals indicative of one or more of:
 cerebral oxygenation,
 blood pressure,
 cerebral blood flow,
 systemic glucose level(s),
 cerebral lactate level(s),
 cerebral glucose level(s),
 cytotoxic edema, and
 excitotoxic activity.

23. A brain rescue instrument according to claim 22 wherein said signal or signals indicative of brain edema include one or more of a signal indicative of brain tissue impedance, a signal indicative of cytotoxic edema, a signal indicative of vasogenic edema, a signal indicative of intracranial pressure, and a signal indicative of cerebral perfusion pressure.

24. A brain rescue instrument according to claim 18 arranged to highlight variations in at least some of the displayed signals or information which are indicative or predictive of secondary phase brain damage.

25. A brain rescue instrument according to claim 18 wherein said computing means is arranged to apply to at least some of the signals or information obtained therefrom expert analytical rules based on knowledge of the behavior of the signals over time during developing secondary phase brain damage, and to display to a user the signals or information obtained therefrom in a way which highlights variations identified by application of said expert analytical rules which are indicative or predictive of secondary phase brain damage or a risk of secondary phase damage.

26. A brain rescue instrument according to claim 3 arranged to highlight variations in at least some of the displayed signals or information which are indicative or predictive of secondary phase brain damage.

27. A brain rescue instrument according to claim 3 wherein said computing means is arranged to apply to at least some of the signals or information obtained therefrom expert analytical rules based on knowledge of the behavior of the signals over time during developing secondary phase brain damage, and to display to a user the signals or information obtained therefrom in a way which highlights variations identified by application of said expert analytical rules which are indicative or predictive of secondary phase brain damage or a risk of secondary phase damage.

28. A brain rescue instrument according to claim 27 wherein said computing means includes software including signal analysis modules arranged to perform initial signal processing and brain rescue task modules arranged to apply said expert analytical rules to data from the signal analysis modules.

29. An intelligent brain rescue instrument according to claim 27 wherein in applying said expert analytical rules said computing means is arranged to compare one or more of said signals or information obtained from said signal(s) against stored information on normal range(s) for said signal(s), and the instrument is arranged to provide an indication to a user if one or more of said signal(s) exceeds said normal range(s).

30. A brain rescue instrument according to claim 27 wherein in applying said expert analytical rules said computing means is arranged to compare at least one combination of more than one signal or information obtained from said signal(s) against stored information on normal ranges for the combination(s) of signals, and the instrument is arranged to provide an indication to a user if the combination (s) of signals exceeds said normal range(s).

31. A brain rescue instrument according to claim 27 wherein in applying said expert analytical rules said computing means is arranged to apply multiple evaluation processes to at least some of the signals.

32. A brain rescue instrument according to claim 27 wherein in applying said expert analytical rules said computing means is arranged to compare one or more signal(s) acquired from a patient or information obtained from said signal(s) to signals previously acquired from the same patient or information obtained therefrom.

33. A brain rescue instrument according to claim 27 arranged to store at least some of said signals or information obtained from at least some of said signals, acquired from a patient over a number of hours.

34. A brain rescue instrument according to claim 27 arranged to store at least some of said signals or information obtained from at least some of said signals, acquired from a patient over one or more days.

35. A brain rescue instrument according to claim 27 arranged to store at least some of said signals or information acquired from a patient over a number of hours or days and to apply said expert analytical rules to said stored signals or information to identify variations in said signals occurring over a number of hours or days.

36. A brain rescue instrument according to claim 27 arranged to apply said expert analytical rules to stored information acquired from a patient over time and to provide an indication to a user of a likely neural outcome for the patient.

37. A brain rescue instrument according to claim 27 including a software based advisor or help system arranged to provide expert advice based on rules or models in the software to assist a clinician.

38. A brain rescue instrument according to claim 27 including stored representative examples of variations of signals or combinations or groups of signals indicative or predictive of secondary phase brain damage, which may be called up by a user.

39. A brain rescue instrument according to claim 1 wherein said computing means is arranged to apply to at least some of the signals or information obtained therefrom expert analytical rules based on knowledge of the behavior of the signals over time during developing secondary phase brain damage, and to display to a user the signals or information obtained therefrom in a way which highlights variations identified by application of said expert analytical rules which are indicative or predictive of secondary phase brain damage or a risk of secondary phase damage.

40. A brain rescue instrument for use in identifying, monitoring, and guiding the application of brain therapies to patients at risk of secondary phase brain damage including delayed neuronal death, comprising:

input means for acquiring a number of signals each indicative of a different biochemical or biophysical parameter of a patient, selection means enabling a user to select between groups of said signals, the behavior of each group of signals over time being indicative or predictive of developing secondary phase damage or a risk thereof, and computing means configured to continuously process and display to a user the selected group of signals or information obtained therefrom on one or more time scales which show variations in the selected signals which are indicative or predictive of secondary phase brain damage or a risk of secondary phase damage.

41. A brain rescue instrument according to claim 40 wherein said groups of signals comprise two or more groups of signals selected from:

(I) a group of signals useful in early prediction of risk of secondary damage, that can aid in the selection of patients for rescue therapy, including an EEG signal or signals and one or more of:
an ECG signal,
a signal indicative of cerebral lactate level(s),
a signal indicative of cerebral oxygen consumption,
a signal or signals obtained from the EEG signal(s) indicative of one or both of seizure and spike activity,
a signal indicative of brain edema,
a signal indicative of cerebrovascular status,
a signal indicative of cerebral haemodynamic status,
a signal indicative of cerebral blood flow, and
a signal indicative of blood pressure;

(II) a group of signals useful in the detection and management of post insult seizures in patients, including an EEG signal or signals; signals obtained from the EEG signal or signals indicative of one or more of (i) one or both of cortical seizure and spike activity, (ii) the level and frequency of background EEG activity, and (iii) the spatial distribution of EEG derived signals; and a signal or signals indicative of one or more of:
movement or muscle activity,
heart rate,
blood pressure,
cerebral blood flow,
cerebral haemodynamic status,
brain edema,
one or more of core body temperature, cerebral temperature, and scalp or skin temperature;

(III) a group of signals useful in patient monitoring during hypothermia therapy, including an EEG signal or signals; a signal or signals indicative of one or more core body temperature; cerebral temperature, and scalp or skin temperature; a signal indicative of heat transfer device function; and a signal or signals indicative of one or more of brain edema and cardiovascular compromise; and (IV) a group of signals useful in monitoring the brain status of patients for signs or secondary phase damage or a risk thereof including an EEG signal or signals; a signal or signals obtained from the EEG signal or signals indicative of one or both of seizure and spike activity; a signal or signals indicative of one or more of core body temperature, cerebral temperature, and scalp or skin temperature; a signal indicative of brain edema; and a signal indicative of one or more of:

cerebral oxygenation,
blood pressure,
cerebral blood flow,
systemic glucose level(s),
cerebral lactate level(s),
cerebral glucose, and
cytotoxic edema.

42. A brain rescue instrument according to claim 41 wherein said group of signals useful in monitoring the brain status of patients comprise a group of signals useful in monitoring the brain status of the evolving or secondary phases or neural injury of patients, including an EEG signal or signals; one or more signals obtained from the EEG signal or signals indicative of one or both of seizure and spike activity; a signal indicative of brain edema; and a signal indicative of one or more of:

cerebral oxygenation,
cerebral blood flow,
cerebral haemodynamic status,
cerebrovascular status,
cerebral lactate level(s),
cytotoxic edema,
cerebral glucose level(s),
excitotoxic activity.

43. A brain rescue instrument according to claim 41 wherein said group of signals useful in monitoring the brain status of patients comprises a group of signals useful in monitoring to predict risk of secondary phase damage to assist with minimization of delayed damage, including an EEG signal or signals; one or more signals obtained from the EEG signal or signals indicative of one or both of seizure and spike activity; a signal indicative of one or more of core body temperature, cerebral temperature, and scalp or skin temperature; a signal indicative of brain edema; and a signal or signals indicative of one or more of:

cerebral oxygenation,
blood pressure,
cerebral blood flow,
systemic glucose level(s),
cerebral lactate level(s),
cerebral glucose level(s),
cytotoxic edema, and
excitotoxic activity.

44. A brain rescue instrument according to claim 41 wherein said signal or signals indicative of brain edema include one or more of a signal indicative of brain tissue impedance, a signal indicative of cytotoxic edema, a signal indicative of vasogenic edema, a signal indicative of intracranial pressure, and a signal indicative of cerebral perfusion pressure.

45. A brain rescue instrument according to claim 41, arranged to highlight variations in at least some of the displayed signals of the selected group which are indicative or predictive of secondary phase brain damage.

46. A brain rescue instrument according to claim 41 wherein said computing means is arranged to apply to at least some of the signals or information obtained therefrom expert analytical rules based on knowledge of the behavior of the signals over time during developing secondary phase brain damage, and to display to a user the signals or information obtained therefrom in a way which highlights variations identified by application of said expert analytical rules which are indicative or predictive of secondary phase brain damage or a risk of secondary phase damage.

47. A brain rescue instrument according to claim 40, arranged to highlight variations in at least some of the displayed signals of the selected group which are indicative or predictive of secondary phase brain damage.

48. A brain rescue instrument according to claim 40 wherein said computing means is arranged to apply to at least some of the signals or information obtained therefrom expert analytical rules based on knowledge of the behavior of the signals over time during developing secondary phase brain damage, and to display to a user the signals or information obtained therefrom in a way which highlights variations identified by application of said expert analytical rules which are indicative or predictive of secondary phase brain damage or a risk of secondary phase damage.

* * * * *